(12) United States Patent
Suzuki et al.

(10) Patent No.: US 8,377,922 B2
(45) Date of Patent: Feb. 19, 2013

(54) BENZAZEPINONE COMPOUND

(75) Inventors: Naoto Suzuki, Ube (JP); Yasunori Tsuzaki, Ube (JP); Kimihiko Yoshimura, Ube (JP); Masahiko Hagihara, Ube (JP); Yukinori Wada, Ube (JP); Masao Maruyama, Ube (JP); Nobuyoshi Fujii, Ube (JP); Yasuhiro Aga, Ube (JP)

(73) Assignee: Ube Industries, Ltd., Ube-Shi, Yamaguchi (JP)

( * ) Notice: Subject to any disclaimer, the term of this patent is extended or adjusted under 35 U.S.C. 154(b) by 0 days.

(21) Appl. No.: 12/743,223

(22) PCT Filed: Nov. 14, 2008

(86) PCT No.: PCT/JP2008/070804
§ 371 (c)(1),
(2), (4) Date: May 14, 2010

(87) PCT Pub. No.: WO2009/063990
PCT Pub. Date: May 22, 2009

(65) Prior Publication Data
US 2010/0249396 A1    Sep. 30, 2010

(30) Foreign Application Priority Data

Nov. 16, 2007  (JP) ................. 2007-297532

(51) Int. Cl.
*C07D 487/04* (2006.01)
*A61K 31/55* (2006.01)

(52) U.S. Cl. .................... 514/212.07; 540/523
(58) Field of Classification Search .......... 540/523; 514/212.07
See application file for complete search history.

(56) References Cited

U.S. PATENT DOCUMENTS

| | | |
|---|---|---|
| 6,514,964 B1 | 2/2003 | Chen et al. |
| 2003/0125317 A1 | 7/2003 | Callahan et al. |
| 2010/0249396 A1 | 9/2010 | Suzuki et al. |

FOREIGN PATENT DOCUMENTS

| | | |
|---|---|---|
| EP | 2 221 308 A1 | 8/2010 |
| JP | 2001-501936 A | 2/2001 |
| JP | 2004-502635 A | 1/2004 |
| JP | 2004-528373 A | 9/2004 |
| WO | WO 96/00574 A1 | 1/1996 |
| WO | WO 96/00730 A1 | 1/1996 |
| WO | WO 98/14192 A1 | 4/1998 |
| WO | WO 98/15278 A1 | 4/1998 |
| WO | WO 99/06049 A1 | 2/1999 |
| WO | WO 99/15170 A1 | 4/1999 |
| WO | WO 99/15178 A1 | 4/1999 |
| WO | WO 00/46215 A1 | 8/2000 |
| WO | WO 01/23357 A2 | 4/2001 |
| WO | WO 02/090325 A2 | 11/2002 |
| WO | WO 03/013511 A1 | 2/2003 |
| WO | WO 2009/063990 A1 | 5/2009 |

OTHER PUBLICATIONS

Azare et al., Molecular and Cellular Biology, vol. 27, No. 12, pp. 4444-4453, Jun. 2007.
Goodman et al., Journal of Medical Chemistry, vol. 45, No. 5, pp. 1045-1051, 2002.
Munger et al., Cell, vol. 96, 319-328, Feb. 5, 1999.
English translation of the International Preliminary Report on Patentability (PCT/IB/338, PCT/IB/373 and PCT/ISA/237) mailed Jul. 8, 2010 in International Application No. PCT/JP2008/070804.
European Search Report dated May 25, 2011in corresponding EP Application No. 08850399.
Ashraf et al., "Angiogenesis in osteoarthritis," Current Opinion in Rheumatology, vol. 20, pp. 573-580, 2008.
Bonnet et al., "Osteoarthritis, angiogenesis and inflammation," Rheumatology, vol. 44, pp. 7-16, 2005.
Brooks et al., "Antiintegrin αvβ3 blocks human breast cancer growth and angiogenesis in human skin," The Journal of Clinical Investigation, vol. 96, pp. 1815-1822, Oct. 1995.

(Continued)

*Primary Examiner* — Bruck Kifle
(74) *Attorney, Agent, or Firm* — Birch, Stewart, Kolasch & Birch, LLP

(57) ABSTRACT

The present invention relates to a benzazepinone compound represented by the following formula (I):

[Formula 1]

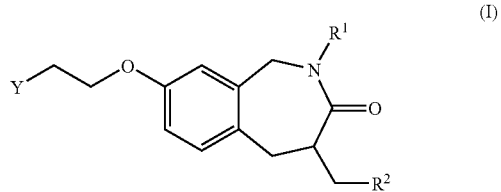

wherein $R^1$ represents a $C_1$-$C_6$ alkyl group or halogeno $C_1$-$C_6$ alkyl group, $R^2$ represents a carboxyl group which may be protected, and Y represents a group represented by the formula (II):

[Formula 2]

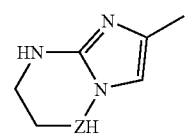

wherein Z represents CH or a nitrogen atom,
or a pharmaceutically acceptable salt thereof.

26 Claims, 1 Drawing Sheet

OTHER PUBLICATIONS

Creamer et al., "Angiogensis in psoriasis," Angiogenesis, vol. 5, pp. 231-236, 2002.

Danese et al., "Angiogenesis as a Novel Component of Inflammatory Bowel Disease Pathogenesis," Gastroenterology, vol. 130, pp. 2060-2073, 2006.

Danese et al., "Angiogenesis blockade as a new therapeutic approach to experimental colitis," Gut Journal, vol. 56, pp. 855-862, 2007.

Engleman et al., "A Peptidomimetic Antagonist of the $\alpha v\beta 3$ Integrin Inhibits Bone Resorption in Vitro and Prevents Osteoporosis In Vivo," The Journal of Clinical Investigation, vol. 99, No. 9, pp. 2284-2292, May 1997.

Hariharan et al., "Assessment of the biological and pharmacological effects of the $\alpha v\beta 3$ and $\alpha v\beta 5$ integrin receptor antagonist, cilengitide (EMD 121974), in patients with advanced solid tumors," Annals of Oncology, vol. 18, pp. 1400-1407, 2007.

Isner, "Cancer and Atherosclerosis : The Broad Mandate of Anglogenesis," Circulation, vol. 99, pp. 1653-1655, 1999.

Koutroubakis et al., "Role of Angiogenesis in Inflammatory Bowel Disease," Inflammatory Bowel Diseases, vol. 12, No. 6, pp. 515-523, Jun. 2006.

Kumar et al., "Inhibition of Angiogenesis and Tumor Growth by SCH221153, a Dual $\alpha v\beta 3$ and $\alpha v\beta 5$ Integrin Receptor Antagonist," Cancer Research vol. 61, pp. 2232-2238, Mar. 1, 2001.

Munger et al., "The Integrin $\alpha v\beta 6$ Binds and Activates Latent TGF$\beta$1: A Mechanism for Regulating Pulmonary Inflammation and Fibrosis," Cell. vol. 96, pp. 319-328, Feb. 5, 1999.

Srivatsa et al., "Selective $\alpha v\beta 3$ integrin blockade potently limits neointimal hyperplasia and lumen stenosis following deep coronary arterial stent injury : Evidence for the functional importance of integrin $\alpha v\beta 3$ and osteopontin expression during neointima formation," Cardio. Res., vol. 36, pp. 408-428, 1997.

Storgard et al., "Decreased angiogenesis and arthritic disease in rabbits treated with an $\alpha v\beta 3$ antagonist," The Journal of Clinical Investigation, vol. 103, No. 1, pp. 47-54, Jan. 1999.

Wilder, "Integrin alpha V beta 3 as a target for treatment of rheumatoid arthritis and related rheumatic diseases," Annals of the Rheumatic Diseases, vol. 61, pp. ll96-ll99, 2002.

Yoshio et al., "TNP-470, an angiogenesis inhibitor, suppresses the progression of peritoneal fibrosis in mouse experimental model," Kidney International, vol. 66, pp. 1677-1685, 2004.

International Search Report and the Written Opinion of the International Searching Authority, dated May 25, 2010, for International Application No. PCT/JP2010/055720 (Forms PCT/ISA/210 and PCT/ISA/237).

Letourneau et al., "Synthesis and Initial Evaluation of Novel, Non-peptidic Antagonists of the $\alpha$v-integrins $\alpha v\beta 3$ and $\alpha v\beta 5$," Bioorganic & Medicinal Chemistry Letters, vol. 19, 2009, pp. 352-355 (available online Nov. 24, 2008).

Santulli et al., "Studies with an Orally Bioavailable $\alpha$v Integrin Antagonist in Animal Models of Ocular Vasculopathy: Retinal Neovascularization in Mice . . . ," The Journal of Pharmacology and Experimental Therapeutics, vol. 324, No. 3, 2008, pp. 894-901 (downloaded on Aug. 9, 2011).

Wilkinson-Berka et al., "SB-267268, a Nonpeptidic Antagonist of $\alpha v\beta 3$ and $\alpha v\beta 5$ Integrins, Reduces Angiogenesis and VEGF Expression in a Mouse Model of Retinopathy of Prematurity," Investigative Ophthalmology & Visual Science, vol. 47, No. 4, Apr. 2006. pp. 1600-1605.

Supplementary European Search Report for European Patent Application No. 10758729.7, dated Aug. 9, 2012.

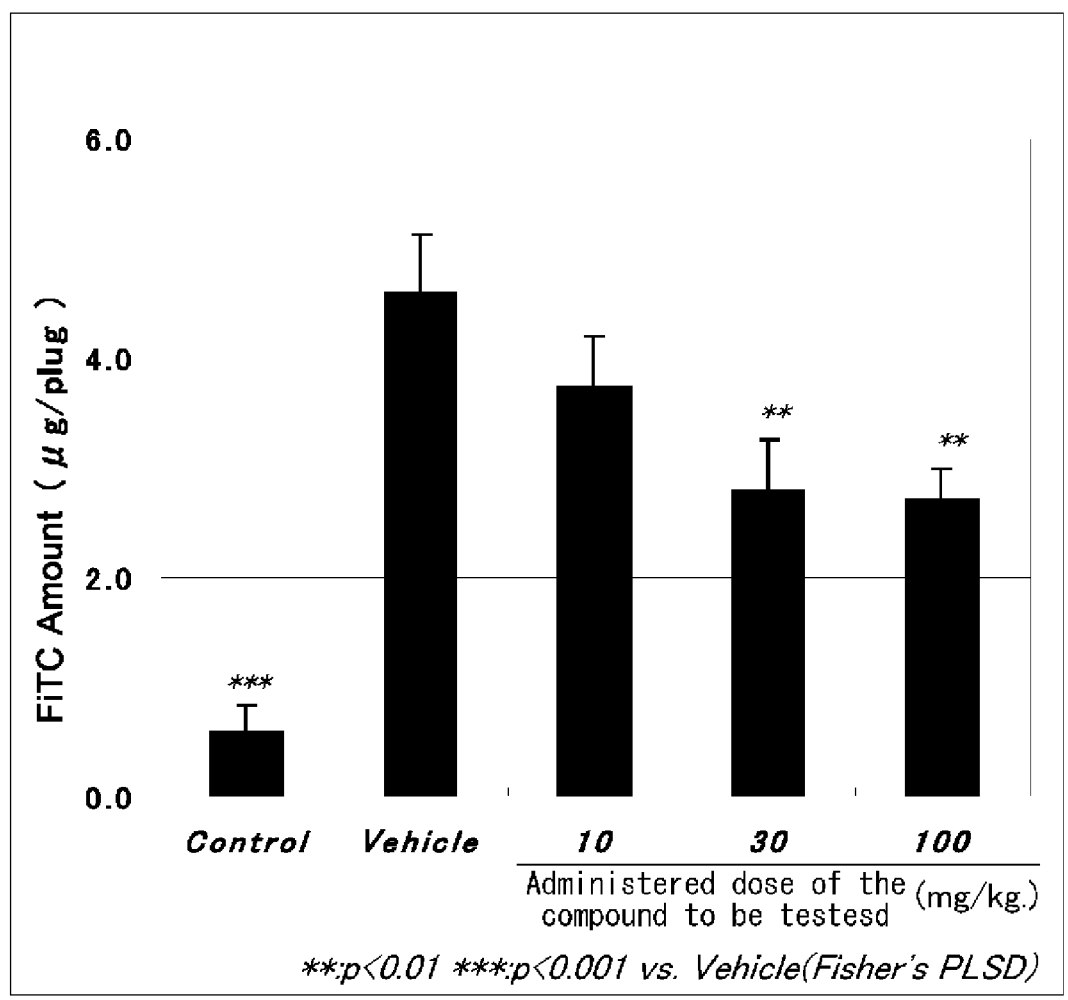

BENZAZEPINONE COMPOUND

TECHNICAL FIELD

The present invention relates to a novel benzazepinone compound and a pharmaceutically acceptable salt thereof useful as a medicine. More specifically, the benzazepinone compound according to the present invention is an antagonist of an αv integrin receptor (in particular, αvβ3, αvβ5 and αvβ6), so that it is useful as a therapeutic agent and/or a prophylactic agent of a disease to which an αv integrin receptor relates, for example, osteoporosis, vascular restenosis, neovascularization, atherosclerosis, inflammatory arthritis, rheumatoid arthritis, cancer, metastatic tumor growth and fibrosis, and other diseases to which an αv integrin receptor relates.

BACKGROUND ART

Integrin is a transmembrane glycoprotein complex of a heterodimer which intermediates cell adhesion and signal transduction process, and comprises an α-subunit and a β-subunit. Relative affinity and specificity for ligand binding are determined by various combination of various α-subunits and β-subunits.

Integrin αvβ3 and αvβ5 are expressed in many cell types, and have been shown to intermediate not only osteoclast adhesion to bone matrix, but also some biologically related processes such as migration, adhesion or proliferation, etc. of vascular smooth muscle cell, tumor cell and endothelial cell, etc. In particular, it has been suggested that it plays a role in various kinds of states and disease states including tumor metastasis, growth of solid tumors (neoplasia), osteoporosis, Paget's disease, humoral hypercalcemia of malignancy, osteopenia, angiogenesis including tumor angiogenesis, arthritis including rheumatoid arthritis, psoriasis and migration of smooth muscle cell (for example, restenosis, arteriosclerosis).

Integrin αvβ6 plays an important part in physiological process and diseases (for example, inflammation, wound healing and tumor) to which epithelial cell relates. In particular, it has been known that the expression of it is increased in lung, skin, kidney, liver, uterus, etc., at the time of sexual cycles or tissue damage due to inflammation, and considered to relate to inflammation, fibrosis, etc. of these internal organs through control of inflammatory cell or cytokine such as TGF-β, etc.

With regard to tumor and fibrosis, not only integrin αvβ6, but also integrin αvβ3 relates thereto, so that to inhibit both of the integrins can be considered to be useful for suppression of tumor and fibrosis. (see Non-Patent Literature 1 to 3)

Heretofore, benzazepinone compounds similar to the compounds of the present invention have been disclosed, and it has been known that these compounds have integrin αvβ3 and αvβ5 inhibitory activity (see Patent Literatures 1 to 8). However, it cannot be said that sufficient effects can be obtained in the points of medicinal efficacy, pharmacokinetics, etc. Also, it has not been specifically disclosed that these compounds have integrin αvβ6 inhibitory activity.

Accordingly, it has been desired to develop non-peptide series low molecular weight compound having further excellent αv integrin receptor antagonistic activity in efficacy, pharmacodynamic characteristics and pharmacokinetic characteristics such as oral bioavailability and duration, etc. Moreover, in either of the above-mentioned literatures, there is no concrete disclosure about a benzazepinone compound having an imidazole ring structure which is ring-fused to a side chain of the benzazepine ring according to the compound of the present invention.

[Non-Patent Literature 1] Cell, 96, 319 (1999)
[Non-Patent Literature 2] J. Med. Chem., 45, 1045 (2002)
[Non-Patent Literature 3] Mol. Cell. Biol., 27, 4444 (2007)
[Patent Literature 1] WO 96/00574A
[Patent Literature 2] WO 96/00730A
[Patent Literature 3] WO 98/14192A
[Patent Literature 4] WO 98/15278A
[Patent Literature 5] WO 99/06049A
[Patent Literature 6] WO 99/15170A
[Patent Literature 7] WO 99/15178A
[Patent Literature 8] WO 02/90325A

DISCLOSURE OF THE INVENTION

Problems to be Solved by the Invention

The present inventors have earnestly studied on the synthesis of a compound(s) having an αv integrin receptor (αvβ3, αvβ5 and αvβ6) antagonistic activity and its pharmacological action, and as a result, they have found that a novel benzazepinone compound has a potent αv integrin receptor antagonistic activity, and has excellent oral absorbability and duration of the effect, whereby the present invention has been accomplished. Accordingly, the present invention is to provide a novel benzazepinone compound having a potent αv integrin receptor antagonistic activity, and excellent oral absorbability and duration of the effect, and a pharmaceutically acceptable salt thereof.

Means to Solve the Problems

The present inventors have studied intensively on a benzazepinone compound, and as a result, they have found that a series of benzazepinone compounds having at the 8-position of a benzazepinone ring an ethoxy group substituted by a specific heteroaryl group, i.e., a series of benzazepinone compounds in which the heteroaryl group has a 5,6,7,8-tetrahydroimidazo[1,2-a]pyrimidin-2-yl group or 1,2,3,4-tetrahydroimidazo[1,2-b][1,2,4]triazin-6-yl group has a potent αv integrin receptor (particularly, αvβ3, αvβ5 and αvβ6) antagonistic activity, and has excellent oral absorbability and duration of the effect, whereby they have accomplished the present invention.

The "benzazepinone compound" in the present invention means
(1) a compound represented by the following formula (I):

[Formula 1]

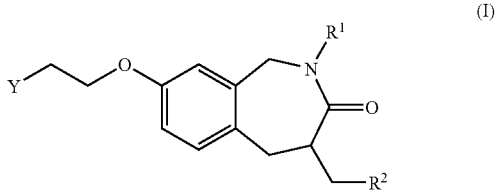

wherein $R^1$ represents a $C_1$-$C_6$ alkyl group or a halogeno $C_1$-$C_6$ alkyl group, $R^2$ represents a carboxyl group which may be protected, Y represents the formula (II):

[Formula 2]

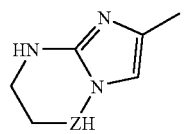

(II)

wherein Z represents CH or a nitrogen atom,
or a pharmaceutically acceptable salt thereof In the benzazepinone compound represented by the formula (I) of the present invention, it is preferably (2) the compound described in (1) wherein $R^1$ is a $C_1$-$C_4$ alkyl group, fluoro $C_1$-$C_4$ alkyl group or chloro $C_1$-$C_4$ alkyl group, (3) the compound described in (1) wherein $R^1$ is an ethyl group, propyl group, isopropyl group, butyl group, isobutyl group, sec-butyl group, difluoromethyl group, trifluoromethyl group, 2-fluoroethyl group, 2,2-difluoroethyl group, 2,2,2-trifluoroethyl group or 2,2,2-trichloroethyl group, (4) the compound described in (1) wherein $R^1$ is an ethyl group, difluoromethyl group, trifluoromethyl group, 2-fluoroethyl group, 2,2-difluoroethyl group or 2,2,2-trifluoro-ethyl group, (5) the compound described in (1) wherein $R^1$ is an ethyl group, trifluoromethyl group or 2,2,2-trifluoroethyl group, (6) the compound described in (1) wherein $R^2$ is a carboxyl group which may be protected by a $C_1$-$C_{12}$ alkyl group, $C_7$-$C_{18}$ aralkyl group, $C_1$-$C_2$ alkyl group substituted by $C_2$-$C_5$ alkanoyloxy group, $C_1$-$C_2$ alkyl group substituted by ($C_1$-$C_4$ alkoxy)carbonyl-oxy group, N,N-dimethylaminocarbonylmethyl group, 2-(morpholin-4-yl)ethyl group, (5-methyl-2-oxo-1,3-dioxolen-4-yl)methyl group or (5-phenyl-2-oxo-1,3-dioxolen-4-yl)methyl group, (7) the compound described in (1) wherein $R^2$ is a carboxyl group which may be protected by a methyl group, ethyl group, propyl group, isopropyl group, 1-ethylpropyl group, butyl group, isobutyl group, sec-butyl group, tert-butyl group, 3,3-dimethylbutyl group, pentyl group, isopentyl group, neopentyl group, tert-pentyl group, 1-methylbutyl group, hexyl group, 1-methylpentyl group, 2-methylpentyl group, 3-methylpentyl group, 1-ethylbutyl group, 2-ethylbutyl group, heptyl group, octyl group, nonyl group, decyl group, undecyl group, dodecyl group, benzyl group, phenethyl group, phenyl-propyl group, phenylbutyl group, phenylpentyl group, phenylhexyl group, phenylheptyl group, phenyloctyl group, phenylnonyl group, phenyldecyl group, phenylundecyl group, phenyldodecyl group, acetoxymethyl group, 1-acetoxyethyl group, pivaloyloxymethyl group, 1-pivaloyloxyethyl group, ethoxycarbonyloxymethyl group, 1-ethoxycarbonyl-oxyethyl group, N,N-dimethylaminocarbonylmethyl group, 2-(morpholin-4-yl)ethyl group or (5-methyl-2-oxo-1,3-dioxolen-4-yl)methyl group, (8) the compound described in (1) wherein $R^2$ is a carboxyl group which may be protected by a methyl group, ethyl group, propyl group, isopropyl group, 1-ethylpropyl group, butyl group, 3,3-dimethylbutyl group, pentyl group, hexyl group, heptyl group, octyl group, nonyl group, decyl group, undecyl group, dodecyl group, benzyl group, phenethyl group, phenylpropyl group, phenylbutyl group, phenylpentyl group, phenylhexyl group, phenylheptyl group, phenyloctyl group, phenylnonyl group, phenyldecyl group, phenylundecyl group, phenyldodecyl group, acetoxymethyl group, pivaloyloxymethyl group, 1-pivaloyloxyethyl group, N,N-dimethylaminocarbonyl-methyl group, 2-(morpholin-4-yl)ethyl group or (5-methyl-2-oxo-1,3-dioxolen-4-yl)methyl group.

(9) the compound described in (1) wherein $R^2$ is a carboxyl group which may be protected by an ethyl group, propyl group, isopropyl group, butyl group, pentyl group, hexyl group, heptyl group, octyl group, nonyl group, decyl group, undecyl group, benzyl group, 2-phenethyl group, 3-phenylpropyl group, 4-phenylbutyl group, 5-phenylpentyl group, 6-phenylhexyl group, 7-phenylheptyl group, 8-phenyloctyl group, 9-phenylnonyl group, 10-phenyldecyl group, pivaloyloxymethyl group, N,N-dimethyl-aminocarbonylmethyl group, 2-(morpholin-4-yl)ethyl group or (5-methyl-2-oxo-1,3-dioxolen-4-yl)methyl group.

Also, in the above-mentioned groups of (2)-(5), (6)-(9), a larger number shows more preferred compounds, and compounds obtained by electing $R^1$ from the groups (2)-(5), and electing $R^2$ from the groups (6)-(9), or, these are optionally combined are preferred compounds.

For example, there may be mentioned

(10) the benzazepinone compound described in (1) wherein $R^1$ is a $C_1$-$C_4$ alkyl group, fluoro $C_1$-$C_4$ alkyl group or chloro $C_1$-$C_4$ alkyl group, $R^2$ is a carboxyl group which may be protected by a $C_1$-$C_{12}$ alkyl group, $C_7$-$C_{18}$ aralkyl group, $C_1$-$C_2$ alkyl group substituted by $C_2$-$C_5$ alkanoyloxy group, $C_1$-$C_2$ alkyl group substituted by ($C_1$-$C_4$ alkoxy)carbonyloxy group, N,N-dimethylaminocarbonyl-methyl group, 2-(morpholin-4-yl)ethyl group, (5-methyl-2-oxo-1,3-dioxolen-4-yl)-methyl group or (5-phenyl-2-oxo-1,3-dioxolen-4-yl)methyl group, and Y is the formula (II),

(11) the benzazepinone compound described in (1) wherein $R^1$ is an ethyl group, propyl group, isopropyl group, butyl group, isobutyl group, sec-butyl group, difluoromethyl group, trifluoromethyl group, 2-fluoroethyl group, 2,2-difluoroethyl group, 2,2,2-tri-fluoroethyl group or 2,2,2-trichloroethyl group, $R^2$ is a carboxyl group which may be protected by a methyl group, ethyl group, propyl group, isopropyl group, 1-ethylpropyl group, butyl group, isobutyl group, sec-butyl group, tert-butyl group, 3,3-dimethylbutyl group, pentyl group, isopentyl group, neopentyl group, tert-pentyl group, 1-methylbutyl group, hexyl group, 1-methylpentyl group, 2-methylpentyl group, 3-methylpentyl group, 1-ethylbutyl group, 2-ethylbutyl group, heptyl group, octyl group, nonyl group, decyl group, undecyl group, dodecyl group, benzyl group, phenethyl group, phenylpropyl group, phenylbutyl group, phenylpentyl group, phenylhexyl group, phenylheptyl group, phenyloctyl group, phenylnonyl group, phenyldecyl group, phenylundecyl group, phenyldodecyl group, acetoxymethyl group, 1-acetoxyethyl group, pivaloyloxymethyl group, 1-pivaloyloxy-ethyl group, ethoxycarbonyloxymethyl group, 1-ethoxycarbonyloxyethyl group, N,N-dimethylaminocarbonylmethyl group, 2-(morpholin-4-yl)ethyl group or (5-methyl-2-oxo-1,3-dioxolen-4-yl)methyl group, and Y is the formula (II),

(12) the benzazepinone compound described in (1) wherein $R^1$ is an ethyl group, difluoromethyl group, trifluoromethyl group, 2-fluoroethyl group, 2,2-difluoroethyl group or 2,2,2-trifluoroethyl group, $R^2$ is a carboxyl group which may be protected by a methyl group, ethyl group, propyl group, isopropyl group, 1-ethylpropyl group, butyl group, 3,3-dimethylbutyl group, pentyl group, hexyl group, heptyl group, octyl group, nonyl group, decyl group, undecyl group, dodecyl group, benzyl group, phenethyl group, phenylpropyl group, phenylbutyl group, phenylpentyl group, phenylhexyl group, phenylheptyl group, phenyloctyl group, phenylnonyl group, phenyldecyl group, phenylundecyl group, phenyldodecyl group, acetoxymethyl group, pivaloyloxymethyl group, 1-pivaloyl-oxyethyl group, N,N-dimethylaminocarbonylmethyl group, 2-(morpholin-4-yl)ethyl group or (5-methyl-2-oxo-1,3-dioxolen-4-yl)methyl group, and Y is the formula (II),

(13) the benzazepinone compound described in (1) wherein
R$^1$ is an ethyl group, trifluoromethyl group or 2,2,2-trifluoroethyl group, R$^2$ is a carboxyl group which may be protected by an ethyl group, propyl group, isopropyl group, butyl group, pentyl group, hexyl group, heptyl group, octyl group, nonyl group, decyl group, undecyl group, benzyl group, 2-phenethyl group, 3-phenylpropyl group, 4-phenylbutyl group, 5-phenylpentyl group, 6-phenylhexyl group, 7-phenylheptyl group, 8-phenyloctyl group, 9-phenylnonyl group, 10-phenyldecyl group, pivaloyloxymethyl group, N,N-dimethylaminocarbonylmethyl group, 2-(morpholin-4-yl)ethyl group or (5-methyl-2-oxo-1,3-dioxolen-4-yl)methyl group, and Y is the formula (II).

In the present invention, the benzazepinone compound represented by the formula (I) or a pharmaceutically acceptable salt thereof is preferably a benzazepinone compound represented by the following formula (III):

[Formula 3]

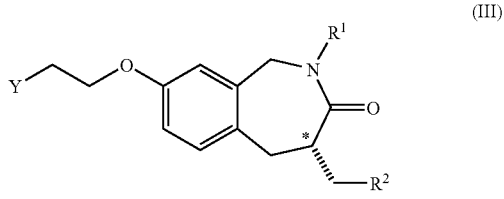

(III)

wherein the carbon atom to which * is attached has a steric configuration (S), and R$^1$, R$^2$ and Y have the same meanings as defined above, or a pharmaceutically acceptable salt thereof In the present invention, as preferred compounds having the formula (I), there may be mentioned, 2-ethyl-3-oxo-8-[2-(5,6,7,8-tetrahydroimidazo[1,2-a]pyrimidin-2-yl)ethoxy]-2,3,4,5-tetrahydro-1H-2-benzazepin-4-acetic acid, 3-oxo-2-propyl-8-[2-(5,6,7,8-tetrahydroimidazo[1,2-a]pyrimidin-2-yl)ethoxy]-2,3,4,5-tetrahydro-1H-2-benzazepin-4-acetic acid, 2-isopropyl-3-oxo-8-[2-(5,6,7,8-tetrahydroimidazo[1,2-a]pyrimidin-2-yl)ethoxy]-2,3,4,5-tetrahydro-1H-2-benzazepin-4-acetic acid, 2-butyl-3-oxo-8-[2-(5,6,7,8-tetrahydroimidazo[1,2-a]pyrimidin-2-yl)ethoxy]-2,3,4,5-tetrahydro-1H-2-benzazepin-4-acetic acid, 2-isobutyl-3-oxo-8-[2-(5,6,7,8-tetrahydroimidazo[1,2-a]pyrimidin-2-yl)ethoxy]-2,3,4,5-tetrahydro-1H-2-benzazepin-4-acetic acid, 2-(sec-butyl)-3-oxo-8-[2-(5,6,7,8-tetrahydroimidazo[1,2-a]pyrimidin-2-yl)ethoxy]-2,3,4,5-tetrahydro-1H-2-benzazepin-4-acetic acid, 2-difluoromethyl-3-oxo-8-[2-(5,6,7,8-tetrahydroimidazo[1,2-a]pyrimidin-2-yl)ethoxy]-2,3,4,5-tetrahydro-1H-2-benzazepin-4-acetic acid, 3-oxo-8-[2-(5,6,7,8-tetrahydroimidazo[1,2-a]pyrimidin-2-yl)ethoxy]-2-trifluoromethyl-2,3,4,5-tetrahydro-1H-2-benzazepin-4-acetic acid, 2-(2-fluoroethyl)-3-oxo-8-[2-(5,6,7,8-tetrahydroimidazo[1,2-a]pyrimidin-2-yl)ethoxy]-2,3,4,5-tetrahydro-1H-2-benzazepin-4-acetic acid, 2-(2,2-difluoroethyl)-3-oxo-8-[2-(5,6,7,8-tetrahydroimidazo[1,2-a]pyrimidin-2-yl)-ethoxy]-2,3,4,5-tetrahydro-1H-2-benzazepin-4-acetic acid, 3-oxo-8-[2-(5,6,7,8-tetrahydroimidazo[1,2-a]pyrimidin-2-yl)ethoxy]-2-(2,2,2-trifluoro-ethyl)-2,3,4,5-tetrahydro-1H-2-benzazepin-4-acetic acid, 3-oxo-8-[2-(5,6,7,8-tetrahydroimidazo[1,2-a]pyrimidin-2-yl)ethoxy]-2-(2,2,2-trichloro-ethyl)-2,3,4,5-tetrahydro-1H-2-benzazepin-4-acetic acid, 2-ethyl-3-oxo-8-[2-(1,2,3,4-tetrahydroimidazo[1,2-b][1,2,4]triazin-6-yl)ethoxy]-2,3,4,5-tetrahydro-1H-2-benzazepin-4-acetic acid, 3-oxo-2-propyl-8-[2-(1,2,3,4-tetrahydroimidazo[1,2-b][1,2,4]triazin-6-yl)ethoxy]-2,3,4,5-tetrahydro-1H-2-benzazepin-4-acetic acid, 2-isopropyl-3-oxo-8-[2-(1,2,3,4-tetrahydroimidazo[1,2-b][1,2,4]triazin-6-yl)ethoxy]-2,3,4,5-tetrahydro-1H-2-benzazepin-4-acetic acid, 2-butyl-3-oxo-8-[2-(1,2,3,4-tetrahydroimidazo[1,2-b][1,2,4]triazin-6-yl)ethoxy]-2,3,4,5-tetrahydro-1H-2-benzazepin-4-acetic acid, 2-isobutyl-3-oxo-8-[2-(1,2,3,4-tetrahydroimidazo[1,2-b][1,2,4]triazin-6-yl)ethoxy]-2,3,4,5-tetrahydro-1H-2-benzazepin-4-acetic acid, 2-(sec-butyl)-3-oxo-8-[2-(1,2,3,4-tetrahydroimidazo[1,2-b][1,2,4]triazin-6-yl)ethoxy]-2,3,4,5-tetrahydro-1H-2-benzazepin-4-acetic acid, 2-difluoromethyl-3-oxo-8-[2-(1,2,3,4-tetrahydroimidazo[1,2-b][1,2,4]triazin-6-yl)-ethoxy]-2,3,4,5-tetrahydro-1H-2-benzazepin-4-acetic acid, 3-oxo-8-[2-(1,2,3,4-tetrahydroimidazo[1,2-b][1,2,4]triazin-6-yl)ethoxy]-2-trifluoro-methyl-2,3,4,5-tetrahydro-1H-2-benzazepin-4-acetic acid, 2-(2-fluoroethyl)-3-oxo-8-[2-(1,2,3,4-tetrahydroimidazo[1,2-b][1,2,4]triazin-6-yl)-ethoxy]-2,3,4,5-tetrahydro-1H-2-benzazepin-4-acetic acid, 2-(2,2-difluoroethyl)-3-oxo-8-[2-(1,2,3,4-tetrahydroimidazo[1,2-b][1,2,4]triazin-6-yl)ethoxy]-2,3,4,5-tetrahydro-1H-2-benzazepin-4-acetic acid, 3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetic acid, or 3-oxo-8-[2-(1,2,3,4-tetrahydroimidazo[1,2-b][1,2,4]triazin-6-yl)ethoxy]-2-(2,2,2-trichloroethyl)-2,3,4,5-tetrahydro-1H-2-benzazepin-4-acetic acid, or a compound in which the carboxyl group thereof is protected by a protective group (said protective group is a C$_1$-C$_{12}$ alkyl group, C$_7$-C$_{18}$ aralkyl group, C$_1$-C$_2$ alkyl group substituted by C$_2$-C$_5$ alkanoyloxy group, C$_1$-C$_2$ alkyl group substituted by (C$_1$-C$_4$ alkoxy)carbonyloxy group, N,N-dimethylaminocarbonylmethyl group, 2-(morpholin-4-yl)ethyl group, (5-methyl-2-oxo-1,3-dioxolen-4-yl)methyl group or (5-phenyl-2-oxo-1,3-dioxolen-4-yl)methyl group.), more preferably 2-ethyl-3-oxo-8-[2-(5,6,7,8-tetrahydroimidazo[1,2-a]pyrimidin-2-yl)ethoxy]-2,3,4,5-tetrahydro-1H-2-benzazepin-4-acetic acid, 2-difluoromethyl-3-oxo-8-[2-(5,6,7,8-tetrahydroimidazo[1,2-a]pyrimidin-2-yl)ethoxy]-2,3,4,5-tetrahydro-1H-2-benzazepin-4-acetic acid, 3-oxo-8-[2-(5,6,7,8-tetrahydroimidazo[1,2-a]pyrimidin-2-yl)ethoxy]-2-trifluoromethyl-2,3,4,5-tetrahydro-1H-2-benzazepin-4-acetic acid, 2-(2-fluoroethyl)-3-oxo-8-[2-(5,6,7,8-tetrahydroimidazo[1,2-a]pyrimidin-2-yl)ethoxy]-2,3,4,5-tetrahydro-1H-2-benzazepin-4-acetic acid, 2-(2,2-difluoroethyl)-3-oxo-8-[2-(5,6,7,8-tetrahydroimidazo[1,2-a]pyrimidin-2-yl)-ethoxy]-2,3,4,5-tetrahydro-1H-2-benzazepin-4-acetic acid, 3-oxo-8-[2-(5,6,7,8-tetrahydroimidazo[1,2-a]pyrimidin-2-yl)ethoxy]-2-(2,2,2-trifluoro-ethyl)-2,3,4,5-tetrahydro-1H-2-benzazepin-4-acetic acid, 2-ethyl-3-oxo-8-[2-(1,2,3,4-tetrahydroimidazo[1,2-b][1,2,4]triazin-6-yl)ethoxy]-2,3,4,5-tetrahydro-1H-2-benzazepin-4-acetic acid, 2-difluoromethyl-3-oxo-8-[2-(1,2,3,4-tetrahydroimidazo[1,2-b][1,2,4]triazin-6-yl)-ethoxy]-2,3,4,5-tetrahydro-1H-2-benzazepin-4-acetic acid, 3-oxo-8-[2-(1,2,3,4-tetrahydroimidazo[1,2-b][1,2,4]triazin-6-yl)ethoxy]-2-trifluoro-methyl-2,3,4,5-tetrahydro-1H-2-benzazepin-4-acetic acid, 2-(2-fluoroethyl)-3-oxo-8-[2-(1,2,3,4-tetrahydroimidazo[1,2-b][1,2,4]triazin-6-yl)-ethoxy]-2,3,4,5-tetrahydro-1H-2-benzazepin-4-acetic acid, 2-(2,2-difluoroethyl)-3-oxo-8-[2-(1,2,3,4-tetrahydroimidazo[1,2-b][1,2,4]triazin-6-yl)ethoxy]-2,3,4,5-tetrahydro-1H-2-benzazepin-4-acetic acid, or 3-oxo-8-[2-(1,2,3,4-tetrahydroimidazo[1,2-b][1,2,4]triazin-6-yl)ethoxy]-2-(2,2,2-tri-fluoroethyl)-2,3,4,5-tetrahydro-1H-2-benzazepin-4-acetic acid, or a compound in which the carboxyl group thereof is protected by a protective group (said protective group is a methyl group, ethyl group, propyl group, isopropyl group, 1-ethylpropyl group, butyl group, isobutyl group, sec-butyl group, tert-butyl group, 3,3-dimethylbutyl group, pentyl group, isopentyl group, neopentyl group, tert-pentyl group, 1-methylbutyl group, hexyl group, 1-methylpentyl group, 2-methylpentyl group, 3-methylpentyl group, 1-ethylbutyl group, 2-ethylbutyl group, heptyl group, octyl group, nonyl group, decyl group, undecyl group, dodecyl group, benzyl group, phenethyl group, phenylpropyl group, phenylbutyl group, phenylpentyl group, phenylhexyl group, phenylheptyl group, phenyloctyl group, phenylnonyl group, phenyldecyl group, phenylundecyl group, phenyldodecyl group, acetoxymethyl group, 1-acetoxyethyl group, pivaloyloxymethyl group, 1-pivaloyloxyethyl group, ethoxycarbonyloxymethyl group, 1-ethoxycarbonyloxyethyl group, N,N-dimethylaminocarbonylmethyl group, 2-(morpholin-4-yl)ethyl group or (5-methyl-2-oxo-1,3-dioxolen-4-yl)methyl group.), further more preferably 2-ethyl-3-oxo-8-[2-(5,6,7,8-tetrahydroimidazo[1,2-a]pyrimidin-2-yl)ethoxy]-2,3,4,5-tetrahydro-1H-2-benzazepin-4-acetic acid, (4S)-2-ethyl-3-oxo-8-[2-(5,6,7,8-tetrahydroimidazo[1,2-a]pyrimidin-2-yl)ethoxy]-2,3,4,5-tetrahydro-1H-2-benzazepin-4-acetic acid, 3-oxo-8-[2-(5,6,7,8-tetrahydroimidazo[1,2-a]pyrimidin-2-yl)ethoxy]-2-trifluoromethyl-2,3,4,5-tetrahydro-1H-2-benzazepin-4-acetic acid, (4S)-3-oxo-8-[2-(5,6,7,8-tetrahydroimidazo[1,2-a]pyrimidin-2-yl)ethoxy]-2-trifluoro-methyl-2,3,4,5-tetrahydro-1H-2-benzazepin-4-acetic acid, 3-oxo-8-[2-(5,6,7,8-tetrahydroimidazo[1,2-a]pyrimidin-2-yl)ethoxy]-2-(2,2,2-trifluoro-ethyl)-2,3,4,5-tetrahydro-1H-2-benzazepin-4-acetic acid, (4S)-3-oxo-8-[2-(5,6,7,8-tetrahydroimidazo[1,2-a]pyrimidin-2-yl)ethoxy]-2-(2,2,2-tri-fluoroethyl)-2,3,4,5-tetrahydro-1H-2-benzazepin-4-acetic acid, 2-ethyl-3-oxo-8-[2-(1,2,3,4-tetrahydroimidazo[1,2-b][1,2,4]triazin-6-yl)ethoxy]-2,3,4,5-tetrahydro-1H-2-benzazepin-4-acetic acid, (4S)-2-ethyl-3-oxo-8-[2-(1,2,3,4-tetrahydroimidazo[1,2-b][1,2,4]triazin-6-yl)ethoxy]-2,3,4,5-tetrahydro-1H-2-benzazepin-4-acetic acid, 3-oxo-8-[2-(1,2,3,4-tetrahydroimidazo[1,2-b][1,2,4]triazin-6-yl)ethoxy]-2-trifluoro-methyl-2,3,4,5-tetrahydro-1H-2-benzazepin-4-acetic acid, (4S)-3-oxo-8-[2-(1,2,3,4-tetrahydroimidazo[1,2-b][1,2,4]triazin-6-yl)ethoxy]-2-tri-fluoromethyl-2,3,4,5-tetrahydro-1H-2-benzazepin-4-acetic acid, 3-oxo-8-[2-(1,2,3,4-tetrahydroimidazo[1,2-b][1,2,4]triazin-6-yl)ethoxy]-2-(2,2,2-tri-fluoroethyl)-2,3,4,5-tetrahydro-1H-2-benzazepin-4-acetic acid, or (4S)-3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetic acid, or a compound in which the carboxyl group thereof is protected by a protective group (said protective group is a methyl group, ethyl group, propyl group, isopropyl group, 1-ethylpropyl group, butyl group, 3,3-dimethylbutyl group, pentyl group, hexyl group, heptyl group, octyl group, nonyl group, decyl group, undecyl group, dodecyl group, benzyl group, phenethyl group, phenylpropyl group, phenylbutyl group, phenylpentyl group, phenylhexyl group, phenylheptyl group, phenyloctyl group, phenylnonyl group, phenyldecyl group, phenylundecyl group, phenyldodecyl group, acetoxymethyl group, pivaloyloxymethyl group, 1-pivaloyloxyethyl group, N,N-dimethylaminocarbonyl-methyl group, 2-(morpholin-4-yl)ethyl group or (5-methyl-2-oxo-1,3-dioxolen-4-yl)-methyl group.), particularly preferably 3-oxo-8-[2-(5,6,7,8-tetrahydroimidazo[1,2-a]pyrimidin-2-yl)ethoxy]-2-(2,2,2-trifluoro-ethyl)-2,3,4,5-tetrahydro-1H-2-benzazepin-4-acetic acid, (4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetic acid, ethyl 3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate, ethyl(4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate, propyl 3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate, propyl (4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate, isopropyl 3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate, isopropyl (4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate, heptyl 3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate, heptyl (4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate, undecyl 3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate, undecyl (4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate, benzyl 3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate, benzyl (4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate, (10-phenyl)decyl 3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate, (10-phenyl)decyl (4S)-3-oxo-8-[2-(5,6,7,8-tetrahydroimidazo[1,2-a]pyrimidin-2-yl)-ethoxy]-2-(2,2,2-trifluoroethyl)-2,3,4,5-tetrahydro-1H-2-benzazepin-4-acetate, pivaloyloxymethyl 3-oxo-8-[2-(5,6,7,8-tetrahydroimidazo[1,2-a]pyrimidin-2-yl)-ethoxy]-2-(2,2,2-trifluoroethyl)-2,3,4,5-tetrahydro-1H-2-benzazepin-4-acetate, pivaloyloxymethyl(4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate, (N,N-dimethylaminocarbonyl)methyl 3-oxo-8-[2-(5,6,7,8-tetrahydroimidazo[1,2-a]-pyrimidin-2-yl)ethoxy]-2-(2,2,2-trifluoroethyl)-2,3,4,5-tetrahydro-1H-2-benzazepin-4-acetate, (N,N-dimethylaminocarbonyl)methyl(4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate,

[2-(morpholin-4-yl)]ethyl 3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate,

[2-(morpholin-4-yl)]ethyl(4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate, (5-methyl-2-oxo-1,3-dioxolen-4-yl)methyl 3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate, (5-methyl-2-oxo-1,3-dioxolen-4-yl)methyl(4S)-3-oxo-8-[2-(5,6,7,8-tetrahydro-imidazo[1,2-a]pyrimidin-2-yl)ethoxy]-2-(2,2,2-trifluoroethyl)-2,3,4,5-tetrahydro-1H-2-benzazepin-4-acetate, 3-oxo-8-[2-(1,2,3,4-tetrahydroimidazo[1,2-b][1,2,4]triazin-6-yl)ethoxy]-2-(2,2,2-tri-fluoroethyl)-2,3,4,5-tetrahydro-1H-2-benzazepin-4-acetic acid, (4S)-3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetic acid, ethyl 3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, ethyl(4S)-3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, propyl 3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, propyl (4S)-3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, isopropyl 3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, isopropyl (4S)-3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, heptyl 3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, heptyl (4S)-3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, undecyl 3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, undecyl (4S)-3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, benzyl 3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, benzyl (4S)-3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, (10-phenyl)decyl 3-oxo-8-[2-(1,2,3,4-tetrahydroimidazo[1,2-b][1,2,4]triazin-6-yl)-ethoxy]-2-(2,2,2-trifluoroethyl)-2,3,4,5-tetrahydro-1H-2-benzazepin-4-acetate, (10-phenyl)decyl (4S)-3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, pivaloyloxymethyl 3-oxo-8-[2-(1,2,3,4-tetrahydroimidazo[1,2-b][1,2,4]triazin-6-yl)-ethoxy]-2-(2,2,2-trifluoroethyl)-2,3,4,5-tetrahydro-1H-2-benzazepin-4-acetate, pivaloyloxymethyl(4S)-3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, (N,N-dimethylaminocarbonyl)methyl 3-oxo-8-[2-(1,2,3,4-tetrahydroimidazo[1,2-b]-[1,2,4]triazin-6-yl)ethoxy]-2-(2,2,2-trifluoroethyl)-2,3,4,5-tetrahydro-1H-2-benzazepin-4-acetate, (N,N-dimethylaminocarbonyl)methyl(4S)-3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate,

[2-(morpholin-4-yl)]ethyl 3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate,

[2-(morpholin-4-yl)]ethyl(4S)-3-oxo-8-[2-(1,2,3,4-tetrahydroimidazo[1,2-b][1,2,4]-triazin-6-yl)ethoxy]-2-(2,2,2-trifluoroethyl)-2,3,4,5-tetrahydro-1H-2-benzazepin-4-acetate, (5-methyl-2-oxo-1,3-dioxolen-4-yl)methyl 3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, or (5-methyl-2-oxo-1,3-dioxolen-4-yl)methyl(4S)-3-oxo-8-[2-(1,2,3,4-tetrahydro-imidazo[1,2-b][1,2,4]triazin-6-yl)ethoxy]-2-(2,2,2-trifluoroethyl)-2,3,4,5-tetrahydro-1H-2-benzazepin-4-acetate.

EFFECTS OF THE INVENTION

The benzazepinone compound represented by the formula (I) or a pharmaceutically acceptable salt thereof of the present invention has excellent characteristics in the points of solubility, oral absorbability, concentration in blood, metabolic stability, tissue distribution, bioavailability (bioavailability; BA), in vitro activity, in vivo activity, rapidness in appearing medicinal effects, duration of medicinal effects, physical stability, drug-drug interaction, toxicity, etc., and further, it shows excellent αv integrin receptor (particularly, αvβ3, αvβ5 and αvβ6) antagonistic activity. Thus, according to the present invention, it is useful as a prophylactic and therapeutic agent of diseases to which αv integrin receptor (particularly, αvβ3, αvβ5 and αvβ6) relates (for example, osteoporosis, vascular restenosis, arteriosclerosis, dissecting aneurysm, transient ischemic attack, apoplectic stroke, angina pectoris, atherosclerosis, inflammatory arthritis, rheumatoid arthritis, osteoarthritis, psoriasis, ulcerative colitis, Crohn's disease, cancer, metastatic tumor growth, connective tissue overgrowth in organs, fibrosis (in particular, pulmonary fibrosis, cystic fibrosis, skin fibrosis, liver fibrosis, cirrhosis, urethrofibrosis, kidney fibrosis, cardiac fibrosis, infantile endocardial fibrosis, pancreatic fibrosis, obstacle keratinization of skin, scleroderma, multiple sclerosis, sarcoma, wound healing)).

BRIEF EXPLANATION OF THE DRAWING

FIG. 1 It is a graph showing an amount of FITC-dextran extracted from a removed Matrigel in Matrigel angiogenesis test of a control group, Vehicle group and a group to which a compound to be tested is administered.

BEST MODE TO CARRY OUT THE INVENTION

In the compound represented by the above-mentioned formula (I), as the "$C_1$-$C_6$ alkyl group" shown by $R^1$, there may be mentioned, for example, a straight or branched $C_1$-$C_6$ alkyl group such as a methyl group, ethyl group, propyl group, isopropyl group, butyl group, isobutyl group, sec-butyl group, tert-butyl group, pentyl group, isopentyl group, neopentyl group, tert-pentyl group, 1-ethylpropyl group, 1-methylbutyl group, 2-methylbutyl group, 1,2-dimethylpropyl group, hexyl group, 1-methylpentyl group, 2-methylpentyl group, 3-methylpentyl group, 4-methylpentyl group, 1-ethylbutyl group, 2-ethylbutyl group, 1,1-dimethylbutyl group, 2,2-dimethyl-butyl group, 3,3-dimethylbutyl group, 1,2-dimethylbutyl group, 1,3-dimethylbutyl group or 2,3-dimethylbutyl group, preferably a $C_1$-$C_4$ alkyl group, more preferably an ethyl group, propyl group, isopropyl group, butyl group, isobutyl group or sec-butyl group, particularly preferably an ethyl group.

The "halogeno" portion of the "halogeno $C_1$-$C_6$ alkyl group" shown by $R^1$ means a halogen atom, and such a halogen atom may be mentioned, for example, a fluorine atom, chlorine atom, bromine atom or iodine atom, preferably a fluorine atom, chlorine atom or bromine atom, more preferably a fluorine atom or chlorine atom, particularly preferably a fluorine atom.

As the "halogeno $C_1$-$C_6$ alkyl group" shown by $R^1$, there may be mentioned, for example, the above-mentioned "$C_1$-$C_6$ alkyl group" substituted by the above-mentioned 1 or 2 or more halogen atoms such as a fluoromethyl group, chloromethyl group, bromomethyl group, iodomethyl group, difluoromethyl group, dichloromethyl group, dibromomethyl group, diiodomethyl group, trifluoromethyl group, trichloromethyl group, 1-fluoroethyl group, 2-fluoroethyl group, 2-chloroethyl group, 2-bromo-ethyl group, 2,2-difluoroethyl group, 2,2,2-trifluoroethyl group, pentafluoroethyl group, 2,2-dichloroethyl group, 2,2,2-trichloroethyl group, 1-fluoropropyl group, 2-fluoro-propyl group, 3-fluoropropyl group, 3,3,3-trifluoropropyl group, perfluoropropyl group, 1-fluoromethylethyl group, 1-difluoromethylethyl group, 1-trifluoromethylethyl group, 1-fluoro-1-methylethyl group, 4-fluorobutyl group, perfluorobutyl group, 5-fluoropentyl group, perfluoropentyl group, 6-fluorohexyl group or perfluorohexyl group, preferably a fluoro $C_1$-$C_4$ alkyl group or chloro $C_1$-$C_4$ alkyl group, more preferably a difluoromethyl group, trifluoromethyl group, 2-fluoroethyl group, 2,2-difluoroethyl group, 2,2,2-tri-fluoroethyl group or 2,2,2-trichloroethyl group, particularly preferably a trifluoromethyl group or 2,2,2-trifluoroethyl group.

$R^1$ is preferably a $C_1$-$C_4$ alkyl group, fluoro $C_1$-$C_4$ alkyl group or chloro $C_1$-$C_4$ alkyl group, more preferably an ethyl group, propyl group, isopropyl group, butyl group, isobutyl group, sec-butyl group, difluoromethyl group, trifluoromethyl group, 2-fluoroethyl group, 2,2-difluoroethyl group, 2,2,2-trifluoroethyl group or 2,2,2-trichloro-ethyl group, more further preferably an ethyl group, difluoromethyl group, trifluoro-methyl group, 2-fluoroethyl group, 2,2-difluoroethyl group or 2,2,2-trifluoroethyl group, particularly preferably an ethyl group, trifluoromethyl group or 2,2,2-trifluoroethyl group.

As the protective group for the carboxyl group which may be protected shown by $R^2$ in the formula (I), there may be mentioned, for example, a $C_1$-$C_{12}$ alkyl group such as a methyl group, ethyl group, propyl group, isopropyl group, 1-ethylpropyl group, butyl group, isobutyl group, sec-butyl group, tert-butyl group, 3,3-dimethylbutyl group, pentyl group, isopentyl group, neopentyl group, tert-pentyl group, 1-methylbutyl group, hexyl group, 1-methylpentyl group, 2-methylpentyl group, 3-methylpentyl group, 1-ethylbutyl group, 2-ethylbutyl group, heptyl group, octyl group, nonyl group, decyl group, undecyl group, or dodecyl group; a $C_7$-$C_{18}$ aralkyl group such as a benzyl group, phenethyl group, phenylpropyl group, phenylbutyl group, phenylpentyl group, phenylhexyl group, phenylheptyl group, phenyloctyl group, phenylnonyl group, phenyl-decyl group, phenylundecyl group, or phenyldodecyl group; a $C_1$-$C_4$ alkyl group substituted by a $C_2$-$C_5$ alkanoyloxy group such as an acetoxymethyl group, 1-acetoxy-ethyl group, 1-acetoxypropyl group, 1-acetoxybutyl group, propanoyloxymethyl group, 1-propanoyloxyethyl group, butanoyloxymethyl group, 1-butanoyloxyethyl group, pivaloyloxymethyl group, 1-pivaloyloxyethyl group, 1-pivaloyloxypropyl group or 1-pivaloyloxybutyl group; a $C_1$-$C_4$ alkyl group substituted by a ($C_1$-$C_4$ alkoxy)carbonyl-oxy group such as a methoxycarbonyloxymethyl group, 1-methoxycarbonyloxyethyl group, ethoxycarbonyloxymethyl group, 1-ethoxycarbonyloxyethyl group, propoxy-carbonyloxymethyl group, 1-propoxycarbonyloxyethyl group, isopropoxycarbonyl-oxymethyl group, 1-isopropoxycarbonyloxyethyl group, butoxycarbonyloxymethyl group, 1-butoxycarbonyloxyethyl group, tert-butoxycarbonyloxymethyl group or 1-tert-butoxycarbonyloxyethyl group; a N,N-dialkylaminocarbonylalkyl group such as a N,N-dimethylaminocarbonylmethyl group or N,N-diethylaminocarbonylmethyl group; a 2-(N,N-dialkylamino)ethyl group such as a 2-(N,N-dimethylamino)ethyl group or 2-(N,N-diethylamino)ethyl group; an alkyl group substituted by a 5-membered or 6-membered hetero-saturated monocyclic ring containing 1 or 2 hetero atom(s) selected from N, O and S such as 2-(morpholin-4-yl)ethyl group, 2-piperidinoethyl group or 2-(4-methyl-piperidino)ethyl group; or a group which can be converted into a carboxyl group by easily deprotected in a living body such as a (5-methyl-2-oxo-1,3-dioxolen-4-yl)methyl group or (5-phenyl-2-oxo-1,3-dioxolen-4-yl)methyl group, etc., preferably a $C_1$-$C_{12}$ alkyl group, $C_7$-$C_{18}$ aralkyl group, $C_1$-$C_2$ alkyl group substituted by $C_2$-$C_5$ alkanoyloxy group, $C_1$-$C_2$ alkyl group substituted by ($C_1$-$C_4$ alkoxy)carbonyloxy group, N,N-dimethylaminocarbonylmethyl group, 2-(morpholin-4-yl)ethyl group, (5-methyl-2-oxo-1,3-dioxolen-4-yl)methyl group or (5-phenyl-2-oxo-1,3-dioxolen-4-yl)methyl group, more preferably a methyl group, ethyl group, propyl group, isopropyl group, 1-ethylpropyl group, butyl group, isobutyl group, sec-butyl group, tert-butyl group, 3,3-dimethylbutyl group, pentyl group, isopentyl group, neopentyl group, tert-pentyl group, 1-methylbutyl group, hexyl group, 1-methylpentyl group, 2-methylpentyl group, 3-methylpentyl group, 1-ethylbutyl group, 2-ethylbutyl group, heptyl group, octyl group, nonyl group, decyl group, undecyl group, dodecyl group, benzyl group, phenethyl group, phenylpropyl group, phenylbutyl group, phenylpentyl group, phenylhexyl group, phenylheptyl group, phenyloctyl group, phenylnonyl group, phenyldecyl group, phenylundecyl group, phenyldodecyl group, acetoxymethyl group, 1-acetoxyethyl group, pivaloyloxymethyl group, 1-pivaloyloxyethyl group, ethoxycarbonyloxymethyl group, 1-ethoxycarbonyloxyethyl group, N,N-dimethylaminocarbonylmethyl group, 2-(morpholin-4-yl)ethyl group or (5-methyl-2-oxo-1,3-dioxolen-4-yl)methyl group, further more preferably a methyl group, ethyl group, propyl group, isopropyl group, 1-ethylpropyl group, butyl group, 3,3-dimethylbutyl group, pentyl group, hexyl group, heptyl group, octyl group, nonyl group, decyl group, undecyl group, dodecyl group, benzyl group, phenethyl group, phenylpropyl group, phenylbutyl group, phenylpentyl group, phenylhexyl group, phenylheptyl group, phenyloctyl group, phenylnonyl group, phenyldecyl group, phenylundecyl group, phenyldodecyl group, acetoxymethyl group, pivaloyloxymethyl group, 1-pivaloyloxyethyl group, N,N-dimethylaminocarbonylmethyl group, 2-(morpholin-4-yl)ethyl group or (5-methyl-2-oxo-1,3-dioxolen-4-yl)methyl group, particularly preferably an ethyl group, propyl group, isopropyl group, butyl group, pentyl group, hexyl group, heptyl group, octyl group, nonyl group, decyl group, undecyl group, benzyl group, 2-phenethyl group, 3-phenylpropyl group, 4-phenylbutyl group, 5-phenylpentyl group, 6-phenylhexyl group, 7-phenylheptyl group, 8-phenyl-octyl group, 9-phenylnonyl group, 10-phenyldecyl group, pivaloyloxymethyl group, N,N-dimethylaminocarbonylmethyl group, 2-(morpholin-4-yl)ethyl group or (5-methyl-2-oxo-1,3-dioxolen-4-yl)methyl group.

Z represents CH or a nitrogen atom.

Y represents a 5,6,7,8-tetrahydroimidazo[1,2-a]pyrimidin-2-yl group or 1,2,3,4-tetrahydroimidazo[1,2-b][1,2,4]triazin-6-yl group.

The compound having the formula (I) of the present invention can be prepared, for example, according to the following methods.

[Method 1]

"Method 1" is a method for generally preparing Compound (Ia) of the present invention wherein $R^2$ in the formula (I) is a carboxyl group.

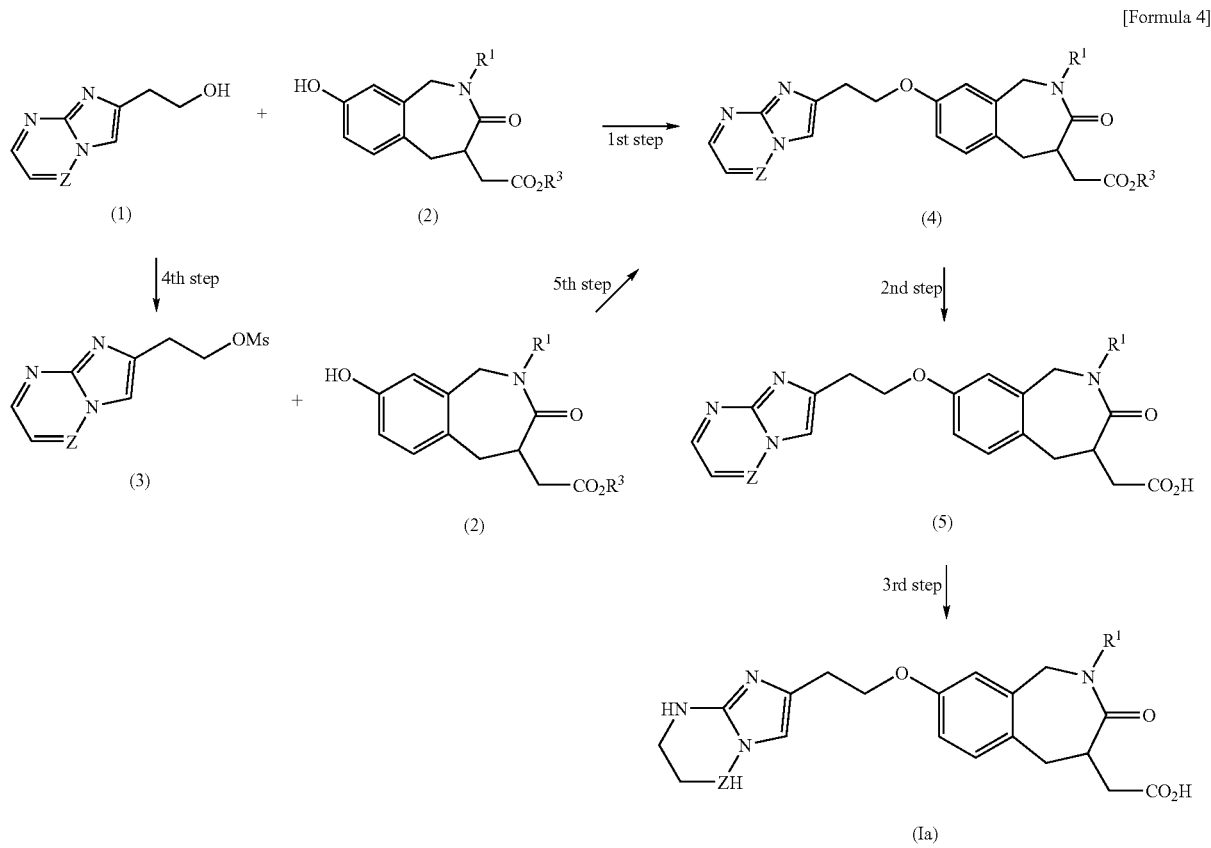

[Formula 4]

wherein $R^1$ and Z have the same meanings as defined above, $R^3$ has the same meaning as the protective group for the carboxyl group which may be protected represented by $R^2$, and Ms represents a methanesulfonyl group.

The first step is a step of preparing Compound (4) by reacting Compound (1) and Compound (2) in an organic solvent by using triphenylphosphine and a condensing agent.

Compound (1) can be prepared according to the method described in, for example, WO97/25325A, and Compound (2) can be prepared according to the method described in, for example, WO98/14192A.

An amount of Compound (1) to be used is generally 1 to 10-fold mol, preferably 1 to 3-fold mol, based on the amount of Compound (2).

As the condensing agent to be used, there may be mentioned diethyl azodi-carboxylate, diisopropyl azodicarboxylate, N,N,N',N'-tetramethylazodicarboxyamide or 1,1'-(azodicarbonyl)dipiperidine, etc., preferably diisopropyl azodicarboxylate.

An amount of the triphenylphosphine to be used is generally 1 to 5-fold mol, preferably 1 to 3-fold mol, based on the amount of Compound (2).

An amount of the condensing agent to be used is generally 1 to 5-fold mol, preferably 1 to 3-fold mol based on the amount of Compound (2).

As the organic solvent to be used, it is not particularly limited so long as it does not inhibit the reaction, and dissolves the starting materials with a certain extent, and there may be mentioned, for example, an ether such as tetrahydrofuran, diethyl ether, diisopropyl ether, ethyleneglycol dimethyl ether, 1,4-dioxane or diglyme, etc.; an aromatic hydrocarbon such as benzene, toluene, xylene, mesitylene or nitrobenzene, etc.; an amide such as N,N-dimethylformamide, N,N-dimethylacetamide, N-methyl-2-pyrrolidone or hexamethylphosphorylamide, etc.; a sulfoxide such as dimethylsulfoxide, etc.; or a mixed solvent thereof, preferably an ether or amide, particularly preferably tetrahydrofuran or N,N-dimethylformamide.

A reaction temperature may vary depending on starting compounds, a reagent or a solvent, etc., and is generally −50° C. to 150° C., preferably −20° C. to 100° C.

A reaction time may vary depending on the reaction temperature, and is generally 1 hour to 48 hours, preferably 1 hour to 24 hours.

The second step is a step of preparing Compound (5) by subjecting Compound (4) to hydrolysis using a base in water, or a mixed solvent of water and an organic solvent.

As the base to be used, there may be mentioned, for example, an inorganic hydroxide such as lithium hydroxide, sodium hydroxide, potassium hydroxide or calcium hydroxide, preferably lithium hydroxide, or sodium hydroxide.

An amount of the base to be used is generally 1 to 100-fold mol, preferably 1 to 50-fold mol based on the amount of Compound (4).

As the solvent to be used, there may be mentioned, for example, water, or a mixed solvent of water and an organic solvent (for example, an alcohol such as methanol, ethanol, propanol, butanol or ethylene glycol, etc.; an ether such as tetra-hydrofuran, diethyl ether, diisopropyl ether, 1,4-dioxane or diglyme, etc.; an amide such as N,N-dimethylformamide, N,N-dimethylacetamide or N-methyl-2-pyrrolidone, etc.; or a sulfoxide such as dimethylsulfoxide, etc., or a mixed solvent of these solvents, preferably an alcohol or ether).

A reaction temperature may vary depending on starting compounds, a reagent or a solvent, etc., and is generally −50° C. to 150° C., preferably −20° C. to 100° C.

A reaction time may vary depending on a reaction temperature, and is generally 1 hour to 24 hours, preferably 1 hour to 12 hours.

The third step is a step of preparing Compound (Ia) of the present invention by carrying out the reaction of Compound (5) in an organic solvent using a reducing agent.

As the reducing agent to be used, there may be mentioned a hydride such as sodium borohydride, lithium borohydride, sodium cyanoborohydride, sodium tri-methoxyborohydride or lithium aluminum hydride, etc., or a metal palladium such as palladium-active carbon or palladium black, etc.; or a metal platinum such as platinum-carbon, etc., in an organic solvent containing hydrogen chloride under hydrogen gas atmosphere, preferably sodium borohydride, or palladium-active carbon under hydrogen gas atmosphere.

An amount of the reducing agent to be used is generally 1 to 100-fold mol, preferably 1 to 50-fold mol based on an amount of Compound (5) when a hydride is used, and is generally 0.01 to 10-fold weight, preferably 0.05 to 5-fold weight when a metal palladium or a metal platinum under hydrogen gas atmosphere is used.

As the organic solvent to be used, it is not particularly limited so long as it does not inhibit the reaction, and dissolves the starting materials with a certain extent, and there may be mentioned, for example, an alcohol such as methanol, ethanol, propanol, butanol or ethylene glycol, etc.; an ether such as tetrahydrofuran, diethyl ether, diisopropyl ether, ethyleneglycol dimethyl ether, 1,4-dioxane or diglyme, etc.; or a mixed solvent of these solvents, preferably methanol, ethanol or tetrahydrofuran.

A reaction temperature may vary depending on starting compounds, a reagent or a solvent, etc., and is generally 0° C. to 150° C., preferably 0° C. to 50° C.

A reaction time may vary depending on a reaction temperature, and is generally 1 hour to 24 hours, preferably 1 hour to 12 hours.

The fourth step and the fifth step are other steps for preparing Compound (4).

The fourth step is a step of preparing Compound (3) by treating Compound (1) and methanesulfonyl chloride with a base in an organic solvent.

As the base to be used, there may be mentioned, for example, an amine such as triethylamine, pyridine, 1,8-diazabicyclo[5.4.0]-7-undecene or diisopropylethylamine, etc.; an inorganic base such as sodium hydride, potassium hydride, potassium carbonate, sodium carbonate, sodium hydrogen carbonate, potassium hydroxide or sodium hydroxide, etc.; or an organic base such as methyl lithium, butyl lithium, lithium diisopropylamide, lithium bistrimethylsilylamide, sodium bistrimethylsilylamide, sodium methoxide, sodium ethoxide or potassium tert-butoxide, etc., preferably triethylamine. An amount of the base to be used is generally 1 to 100-fold mol, preferably 1 to 50-fold mol based on an amount of Compound (1).

An amount of the methanesulfonyl chloride to be used is generally 1 to 50-fold mol, preferably 1 to 10-fold mol based on an amount of Compound (1).

As the organic solvent to be used, it is not particularly limited so long as it does not inhibit the reaction, and dissolves the starting materials with a certain extent, and there may be mentioned, for example, a halogenated hydrocarbon such as dichloro-methane, chloroform or dichloroethane, etc.; an ether such as tetrahydrofuran, diethyl ether, diisopropyl ether, ethyleneglycol dimethyl ether, 1,4-dioxane or diglyme, etc.; or a mixed solvent of these solvents, preferably a halogenated hydrocarbon.

A reaction temperature may vary depending on starting compounds, a reagent or a solvent, etc., and is generally −50° C. to 100° C., preferably −20° C. to 50° C.

A reaction time may vary depending on reaction temperature, and is generally 1 hour to 24 hours, preferably 1 hour to 12 hours.

The fifth step is a step of preparing Compound (4) by treating Compound (3) and Compound (2) with a base in an organic solvent.

As the base to be used, there may be mentioned, for example, an amine such as triethylamine, pyridine, 1,8-diazabicyclo[5.4.0]-7-undecene or diisopropylethylamine, etc.; an inorganic base such as sodium hydride, potassium hydride, potassium carbonate, sodium carbonate, sodium hydrogen carbonate, potassium hydroxide or sodium hydroxide, etc.; or an organic base such as methyl lithium, butyl lithium, lithium diisopropylamide, lithium bistrimethylsilylamide, sodium bistrimethylsilylamide, sodium methoxide, sodium ethoxide or potassium tert-butoxide, etc., preferably sodium hydride. An amount of the base to be used is generally 1 to 10-fold mol, preferably 1 to 5-fold mol based on an amount of Compound (2).

As the organic solvent to be used, it is not particularly limited so long as it does not inhibit the reaction, and dissolves the starting materials with a certain extent, and there may be mentioned, for example, an ether such as tetrahydrofuran, diethyl ether, diisopropyl ether, 1,4-dioxane or diglyme, etc.; an amide such as N,N-dimethylform-amide, N,N-dimethylacetamide or N-methyl-2-pyrrolidone, etc.; a sulfoxide such as dimethylsulfoxide, etc.; or a mixed solvent of these solvents, preferably an ether, particularly preferably tetrahydrofuran.

A reaction temperature may vary depending on starting compounds, a reagent or a solvent, etc., and is generally −50° C. to 150° C., preferably −20° C. to 100° C.

A reaction time may vary depending on a reaction temperature, and is generally 1 hour to 48 hours, preferably 1 hour to 24 hours.

[Method 2]

"Method 2" is another method for preparing Compound (Ib) of the present invention wherein $R^2$ is a protected carboxyl group in the formula (I) and Compound (Ia) of the present invention wherein $R^2$ is a carboxyl group in the same.

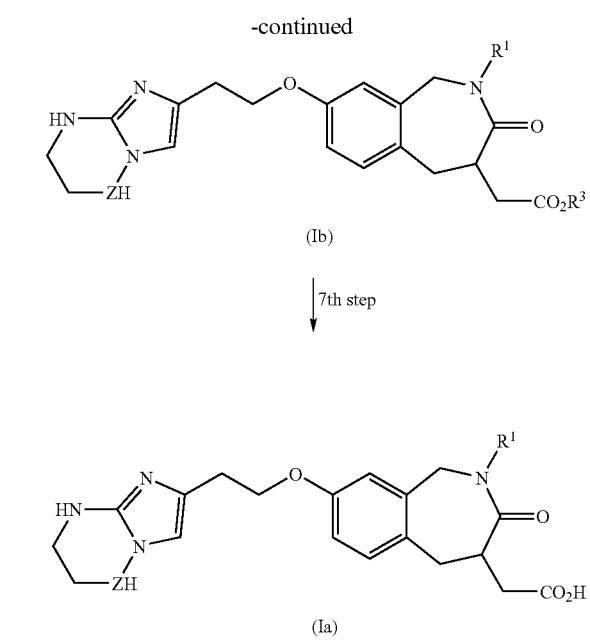

wherein $R^1$, $R^3$ and Z have the same meanings as defined above.

The sixth step is a step of preparing Compound (Ib) of the present invention by reducing Compound (4) in an organic solvent. The present step can be carried out in the same manner as in the above-mentioned "third step" except for using Compound (4) in place of Compound (5).

The seventh step is a step of preparing Compound (Ia) of the present invention by hydrolyzing Compound (Ib) using a base in an organic solvent. The present step can be carried out in the same manner as in the above-mentioned "second step" except for using Compound (Ib) in place of Compound (4).

[Method 3]

"Method 3" is another method for preparing Compound (Ib) of the present invention wherein $R^2$ is a protected carboxyl group in the formula (I) and Compound (Ia) of the present invention wherein $R^2$ is a carboxyl group in the same.

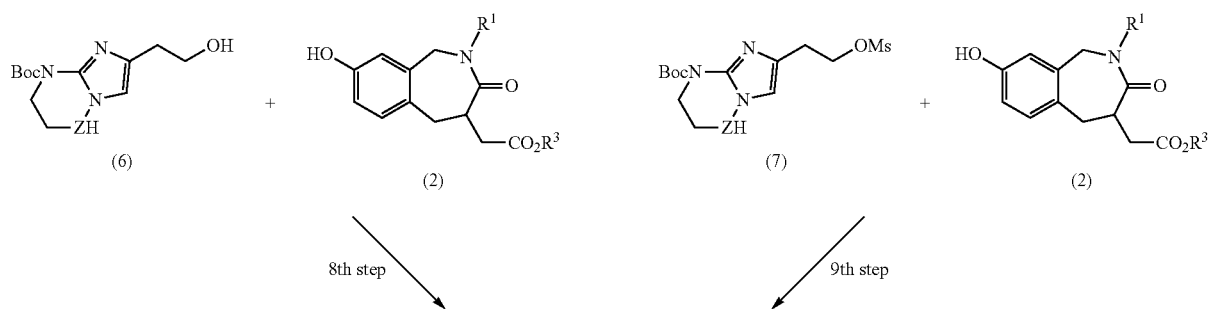

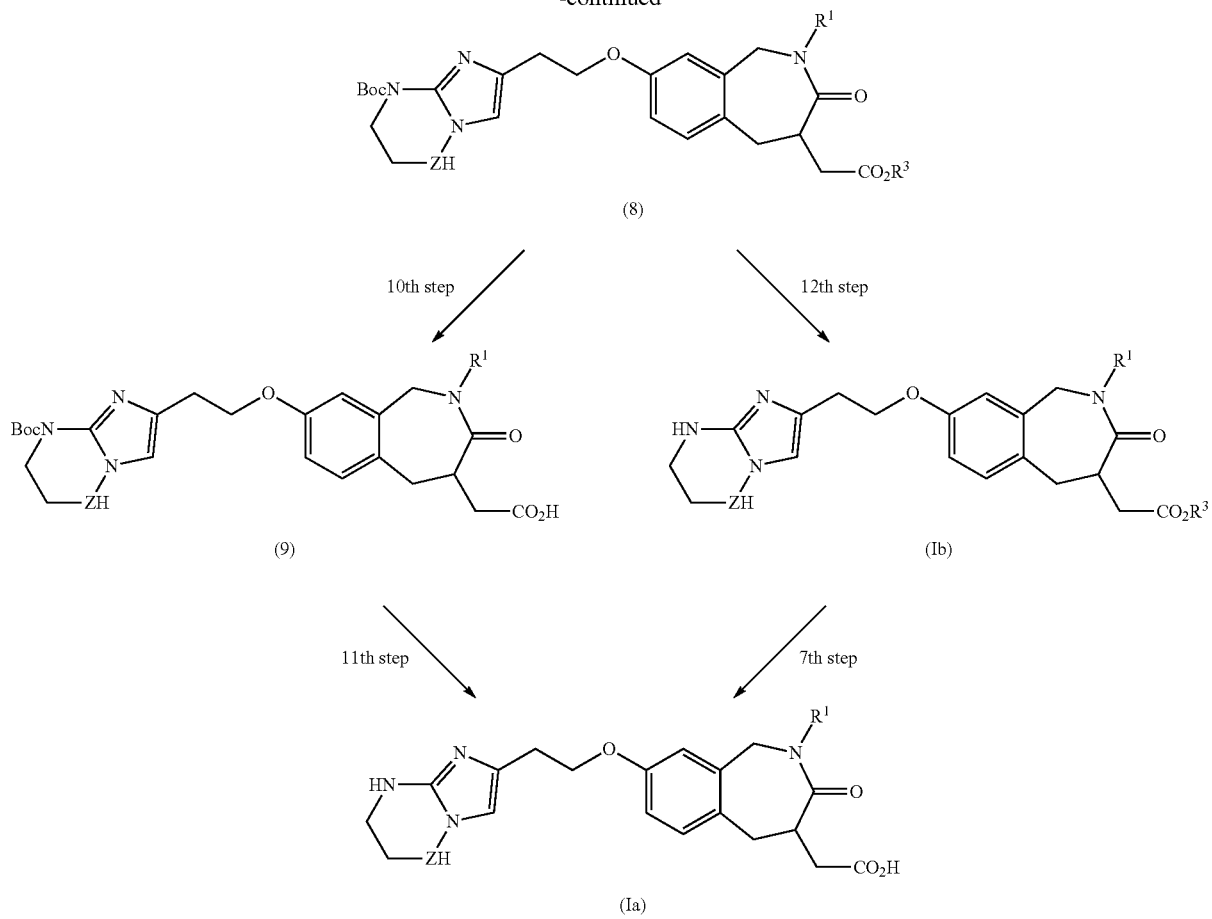

wherein $R^1$, $R^3$, Z and Ms have the same meanings as defined above, and Boc represents a tert-butoxycarbonyl group.

The eighth step is a step of preparing Compound (8) by condensing Compound (6) and Compound (2) in an organic solvent. The present step can be carried out in the same manner as in the above-mentioned "first step" except for using Compound (6) in place of Compound (1). Compound (6) can be prepared by the below mentioned "Method 5".

The ninth step is a step of preparing Compound (8) by treating Compound (7) and Compound (2) with a base in an organic solvent. The present step can be carried out in the same manner as in the above-mentioned "fifth step" except for using Compound (7) in place of Compound (3). Compound (7) can be prepared by the below mentioned "Method 5".

The tenth step is a step of preparing Compound (9) from Compound (8) in water, or in a mixed solvent of water and an organic solvent. The present step can be carried out in the same manner as in the above-mentioned "second step" except for using Compound (8) in place of Compound (4).

The eleventh step is a step of preparing Compound (Ia) of the present invention by treating Compound (9) with an acid in an organic solvent.

As the acid to be used, there may be mentioned, for example, an inorganic acid such as hydrochloric acid, hydrobromic acid, hydroiodic acid, sulfuric acid or nitric acid, etc.; an aliphatic carboxylic acid such as formic acid, acetic acid, propionic acid or butyric acid, etc.; or an organic sulfonic acid such as methanesulfonic acid, benzene-sulfonic acid, p-tolu-enesulfonic acid, naphthalenesulfonic acid or camphorsulfonic acid, etc., preferably an inorganic acid or an aliphatic carboxylic acid. An amount of the acid to be used is generally 1 to 100-fold mol, preferably 1 to 50-fold mol based on an amount of Compound (9).

As the organic solvent to be used, it is not particularly limited so long as it does not inhibit the reaction, and dissolves the starting materials with a certain extent, and there may be mentioned, for example, an alcohol such as methanol, ethanol, propanol, butanol or ethylene glycol, etc.; an ether such as tetrahydrofuran, diethyl ether, diisopropyl ether, 1,4-dioxane or diglyme, etc.; an amide such as N,N-dimethylform-amide, N,N-dimethylacetamide or N-methyl-2-pyrrolidone, etc.; a sulfoxide such as dimethylsulfoxide, etc.; or a mixed solvent of these solvents, preferably an alcohol.

A reaction temperature may vary depending on starting compounds, a reagent or a solvent, etc., and is generally 0° C. to 150° C., preferably 0° C. to 100° C.

A reaction time may vary depending on a reaction temperature, and is generally 1 hour to 72 hours, preferably 1 hour to 48 hours.

The present step may be carried out under an inert gas atmosphere. As the inert gas to be used, there may be mentioned, for example, nitrogen, helium, or argon, etc.

The twelfth step is a step of preparing Compound (Ib) of the present invention by treating Compound (8) with an acid in an organic solvent. The present step can be carried out in the same manner as in the above-mentioned "eleventh step" except for using Compound (8) in place of Compound (9).

By using Compound (Ib) of the present invention obtained in the twelfth step, Compound (Ia) of the present invention can be prepared through the above-mentioned "seventh step".

[Method 4]

"Method 4" is another method for preparing Compound (Ib) of the present invention wherein $R^2$ is a protected carboxyl group in the formula (I).

A reaction time may vary depending on a reaction temperature, and is generally 1 hour to 24 hours, preferably 1 hour to 12 hours.

The present step may be carried out under an inert gas atmosphere. As the inert gas to be used, there may be mentioned, for example, nitrogen, helium, or argon, etc.

[Formula 7]

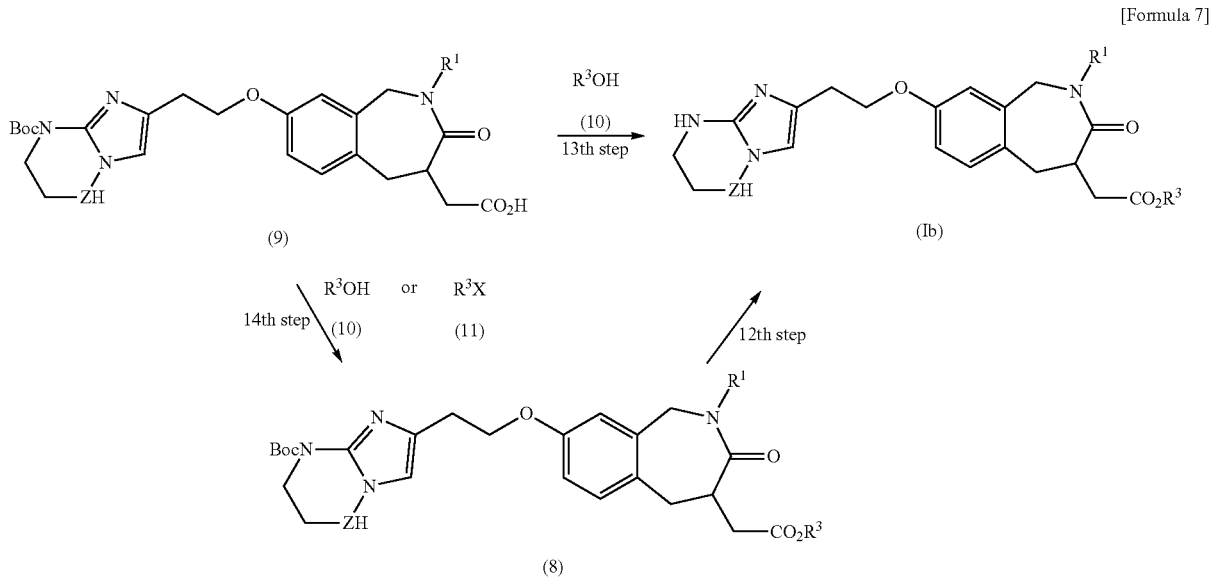

wherein $R^1$, $R^3$, Z and Boc have the same meanings as defined above, and X represents a chlorine atom, bromine atom, or iodine atom.

The thirteenth step is a step of preparing Compound (Ib) by treating Compound (9) and Compound (10) with an acid without solvent or in an organic solvent.

Compound (10) is conventionally known, or can be prepared according to the conventionally known method using the conventionally known compound.

An amount of Compound (10) to be used is generally 1 to 50-fold mol, preferably 1 to 10-fold mol based on an amount of Compound (9), and it may be used with a larger excess amount as a solvent.

As the acid to be used, there may be mentioned an inorganic acid such as hydrochloric acid, hydrobromic acid, hydroiodic acid, sulfuric acid or nitric acid, etc.; or an organic sulfonic acid such as methanesulfonic acid, benzenesulfonic acid, p-toluenesulfonic acid, naphthalenesulfonic acid or camphorsulfonic acid, etc., preferably an inorganic acid. An amount of the acid to be used is generally 1 to 100-fold mol, preferably 1 to 50-fold mol based on an amount of Compound (9).

As the organic solvent to be used, it is not particularly limited so long as it does not inhibit the reaction, and dissolves the starting materials with a certain extent, and there may be mentioned, for example, an ether such as tetrahydrofuran, diethyl ether, diisopropyl ether, 1,4-dioxane or diglyme, etc.; an amide such as N,N-dimethylform-amide, N,N-dimethylacetamide or N-methyl-2-pyrrolidone, etc.; a sulfoxide such as dimethylsulfoxide, etc.; or a mixed solvent of these solvents, preferably an ether.

A reaction temperature may vary depending on starting compounds, a reagent or a solvent, etc., and is generally 0° C. to 150° C., preferably 0° C. to 100° C.

The fourteenth step is a step of preparing Compound (8) by reacting Compound (9) with Compound (10) or Compound (11) in an organic solvent.

Compound (11) is conventionally known, or can be prepared according to the conventionally known method.

When Compound (10) is to be used, the reaction is carried out by using a condensing agent and an additive in an organic solvent, and when Compound (11) is to be used, it can be reacted by using a base in an organic solvent.

When it is to be reacted with Compound (10), as the condensing agent to be used, there may be mentioned dicyclohexylcarbodiimide, diisopropylcarbodiimide, carbonyldiimidazole, N,N'-dicyclohexylcarbodiimide, 1-ethyl-3-(3-dimethylamino-propyl)carbodiimide hydrochloride, 1-[bis (dimethylamino)methylene]-1H-benzotri-azolium-3-oxidehexafluorophosphate, etc., preferably 1-ethyl-3-(3-dimethylamino-propyl)carbodiimide hydrochloride or 1-[bis (dimethylamino)methylene]-1H-benzo-triazolium-3-oxidehexafluorophosphate. An amount of the condensing agent to be used is generally 1 to 10-fold mol, preferably 1 to 3-fold mol based on an amount of Compound (9).

As the additive, there may be mentioned 1-hydroxybenzotriazole or 4-dimethylaminopyridine. An amount of the additive to be used is generally 0.01 to 10-fold mol, preferably 0.1 to 3-fold mol based on an amount of Compound (9).

An amount of Compound (10) to be used is generally 1 to 50-fold mol, preferably 1 to 10-fold mol based on an amount of Compound (9).

As the organic solvent to be used, it is not particularly limited so long as it does not inhibit the reaction, and dissolves the starting materials with a certain extent, and there may be mentioned, for example, a halogenated hydrocarbon such as dichloro-methane, chloroform or dichloroethane, etc.; an ether such as tetrahydrofuran, diethyl ether, diisopropyl ether, ethyleneglycol dimethyl ether, 1,4-dioxane or diglyme, etc.; an amide such as N,N-dimethylformamide, N,N-dimethylacetamide or N-methyl-2-pyrrolidone, etc.; a sulfoxide such as dimethylsulfoxide, etc.; or a mixed solvent of these solvents, preferably a halogenated hydrocarbon, an ether, or an amide, more pre-ferably dichloromethane, tetrahydrofuran or N,N-dimethylformamide.

A reaction temperature may vary depending on starting compounds, a reagent or a solvent, etc., and is generally 0° C. to 150° C., preferably 0° C. to 100° C.

A reaction time may vary depending on a reaction temperature, and is generally 1 hour to 24 hours, preferably 1 hour to 12 hours.

The present reaction may be carried out under an inert gas atmosphere. As the inert gas to be used, there may be mentioned, for example, nitrogen, helium, or argon, etc.

When Compound (11) is to be used, as the base to be used, there may be mentioned, for example, an amine such as triethylamine, pyridine, 1,8-diazabicyclo-[5.4.0]-7-undecene or diisopropylethylamine, etc.; an inorganic base such as sodium hydride, potassium hydride, potassium carbonate, sodium carbonate, sodium hydrogen carbonate, potassium hydroxide or sodium hydroxide, etc.; or an organic base such as methyl lithium, butyl lithium, lithium diisopropylamide, lithium bistrimethylsilylamide, sodium bistrimethylsilylamide, sodium methoxide, sodium ethoxide or potassium tert-butoxide, etc., preferably an inorganic base, more preferably potassium carbonate. An amount of the base to be used is generally 1 to 10-fold mol, preferably 1 to 5-fold mol based on an amount of Compound (9).

An amount of Compound (11) to be used is generally 1 to 10-fold mol, preferably 1 to 5-fold mol based on an amount of Compound (9).

As the organic solvent to be used, it is not particularly limited so long as it does not inhibit the reaction, and dissolves the starting materials with a certain extent, and there may be mentioned, for example, a halogenated hydrocarbon such as dichloro-methane, chloroform or dichloroethane, etc.; an ether such as tetrahydrofuran, diethyl ether, diisopropyl ether, ethyleneglycol dimethyl ether, 1,4-dioxane or diglyme, etc.; an alcohol such as methanol, ethanol, propanol, butanol or ethylene glycol, etc.; an amide such as N,N-dimethylformamide, N,N-dimethylacetamide or N-methyl-2-pyrrolidone, etc.; a sulfoxide such as dimethylsulfoxide, etc.; a nitrile such as acetonitrile, etc.; or a mixed solvent of these solvents, preferably a halogenated hydrocarbon, an amide or a nitrile, more preferably N,N-dimethylformamide.

A reaction temperature may vary depending on starting compounds, a reagent or a solvent, etc., and is generally 0° C. to 150° C., preferably 0° C. to 100° C.

A reaction time may vary depending on a reaction temperature, and is generally 1 hour to 48 hours, preferably 1 hour to 24 hours.

The present reaction may be carried out under an inert gas atmosphere. As the inert gas to be used, there may be mentioned, for example, nitrogen, helium, or argon, etc.

[Method 5]

"Method 5" is a method for preparing Compound (1) in "Method 1", and Compound (6) and Compound (7) in "Method 3".

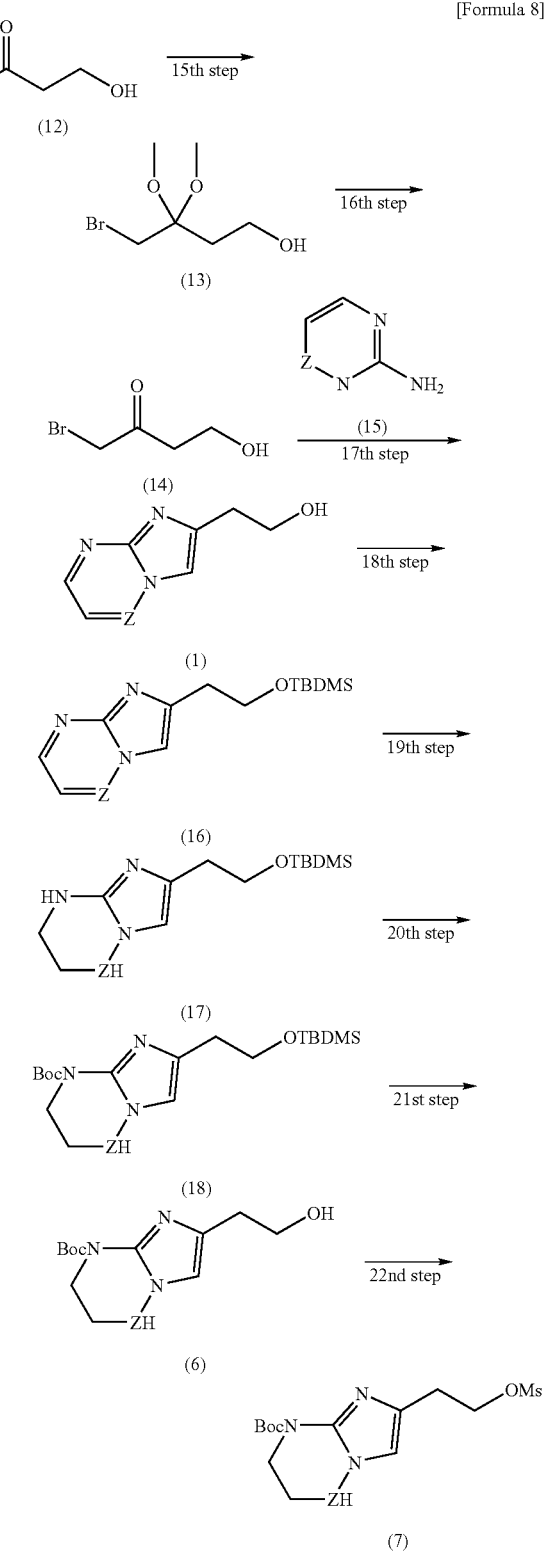

[Formula 8]

wherein Z, Boc, and Ms have the same meanings as defined above, and TBDMS represents a tert-butyldimethylsilyl group.

The fifteenth step is a step of preparing Compound (13) by reacting Compound (12) with a brominating agent in methanol.

As the brominating agent to be used, there may be mentioned, for example, bromine, hydrogen bromide or tetrabutyl ammonium tribromide, etc., preferably bromine. An amount of the brominating agent to be used is generally 1 to 10-fold mol, preferably 1 to 5-fold mol based on an amount of Compound (12).

A reaction temperature may vary depending on starting compounds, a reagent or a solvent, etc., and is generally −50° C. to 150° C., preferably −20° C. to 100° C.

A reaction time may vary depending on a reaction temperature, and is generally 1 hour to 48 hours, preferably 1 hour to 24 hours.

The sixteenth step is a step of preparing Compound (14) by treating Compound (13) with an acid in an organic solvent.

As the acid to be used, there may be mentioned, for example, an inorganic acid such as hydrochloric acid, hydrobromic acid, hydroiodic acid, sulfuric acid or nitric acid, etc.; or an organic sulfonic acid such as methanesulfonic acid, benzenesulfonic acid, p-toluenesulfonic acid, naphthalenesulfonic acid or camphorsulfonic acid, etc., preferably an inorganic acid, particularly preferably sulfuric acid. An amount of the acid to be used is generally 1 to 50-fold mol, preferably 1 to 20-fold mol based on an amount of Compound (13).

As the organic solvent to be used, it is not particularly limited so long as it does not inhibit the reaction, and dissolves the starting materials with a certain extent, and there may be mentioned, for example, an alcohol such as methanol, ethanol, propanol, butanol or ethylene glycol, etc.; an ether such as tetrahydrofuran, diethyl ether, diisopropyl ether, 1,4-dioxane or diglyme, etc.; an amide such as N,N-dimethylform-amide, N,N-dimethylacetamide or N-methyl-2-pyrrolidone, etc.; a sulfoxide such as dimethylsulfoxide, etc.; or a mixed solvent of these solvents, preferably an alcohol.

A reaction temperature may vary depending on starting compounds, a reagent or a solvent, etc., and is generally 0° C. to 150° C., preferably 0° C. to 100° C.

A reaction time may vary depending on a reaction temperature, and is generally 1 hour to 72 hours, preferably 1 hour to 48 hours.

The seventeenth step is a step of preparing Compound (1) by condensing Compound (14) and Compound (15) in an organic solvent.

Compound (15) is conventionally known, or can be prepared according to the conventionally known method using the conventionally known compound. An amount of Compound (15) to be used is generally 1 to 10-fold mol, preferably 1 to 5-fold mol based on an amount of Compound (14).

As the organic solvent to be used, it is not particularly limited so long as it does not inhibit the reaction, and dissolves the starting materials with a certain extent, and there may be mentioned, for example, an alcohol such as methanol, ethanol, propanol, butanol or ethylene glycol, etc.; an ether such as tetrahydrofuran, diethyl ether, diisopropyl ether, 1,4-dioxane or diglyme, etc.; an amide such as N,N-dimethylform-amide, N,N-dimethylacetamide or N-methyl-2-pyrrolidone, etc.; a sulfoxide such as dimethylsulfoxide, etc.; or a mixed solvent of these solvents, preferably an alcohol.

A reaction temperature may vary depending on starting compounds, a reagent or a solvent, etc., and is generally 0° C. to 150° C., preferably 0° C. to 100° C.

A reaction time may vary depending on a reaction temperature, and is generally 1 hour to 48 hours, preferably 1 hour to 24 hours.

The eighteenth step is a step of preparing Compound (16) by treating Compound (1) with an imidazole and tert-butyldimethylsilyl chloride in an organic solvent.

An amount of the imidazole to be used is generally 1 to 50-fold mol, preferably 1 to 10-fold mol based on an amount of Compound (1).

An amount of tert-butyldimethylsilyl chloride to be used is generally 1 to 50-fold mol, preferably 1 to 10-fold mol based on an amount of Compound (1).

As the organic solvent to be used, it is not particularly limited so long as it does not inhibit the reaction, and dissolves the starting materials with a certain extent, and there may be mentioned, for example, a halogenated hydrocarbon such as dichloro-methane, chloroform or dichloroethane, etc.; an ether such as tetrahydrofuran, diethyl ether, diisopropyl ether, ethyleneglycol dimethyl ether, 1,4-dioxane or diglyme, etc.; an amide such as N,N-dimethylformamide, N,N-dimethylacetamide or N-methyl-2-pyrrolidone, etc.; a sulfoxide such as dimethylsulfoxide, etc.; or a mixed solvent of these solvents, preferably an amide.

A reaction temperature may vary depending on starting compounds, a reagent or a solvent, etc., and is generally 0° C. to 100° C., preferably 0° C. to 50° C.

A reaction time may vary depending on a reaction temperature, and is generally 1 hour to 24 hours, preferably 1 hour to 12 hours.

The nineteenth step is a step of preparing Compound (17) by treating Compound (16) with a reducing agent in an organic solvent. The present step can be carried out in the same manner as in the above-mentioned "third step" except for using Compound (16) in place of Compound (5).

The twentieth step is a step of preparing Compound (18) by treating Compound (17) with di-tert-butyl dicarbonate and 4-dimethylaminopyridine in the presence of a base in an organic solvent.

As the base to be used, there may be mentioned, for example, an amine such as triethylamine, pyridine, 1,8-diazabicyclo[5.4.0]-7-undecene or diisopropylethylamine, etc.; an inorganic base such as sodium hydride, potassium hydride, potassium carbonate, sodium carbonate, sodium hydrogen carbonate, potassium hydroxide or sodium hydroxide, etc.; or an organic base such as methyl lithium, butyl lithium, lithium diisopropylamide, lithium bistrimethylsilylamide, sodium bistrimethylsilylamide, sodium methoxide, sodium ethoxide or potassium-tert-butoxide, etc., preferably an amine. An amount of the base to be used is generally 1 to 10-fold mol, preferably 1 to 5-fold mol based on an amount of Compound (17).

An amount of di-tert-butyl dicarbonate to be used is generally 1 to 50-fold mol, preferably 1 to 10-fold mol based on an amount of Compound (17).

An amount of 4-dimethylaminopyridine to be used is generally 0.1 to 5-fold mol, preferably 0.1 to 1-fold mol based on an amount of Compound (17).

As the organic solvent to be used, it is not particularly limited so long as it does not inhibit the reaction, and dissolves the starting materials with a certain extent, and there may be mentioned, for example, a halogenated hydrocarbon such as dichloro-methane, chloroform or dichloroethane, etc.; an ether such as tetrahydrofuran, diethyl ether, diisopropyl ether, ethyleneglycol dimethyl ether, 1,4-dioxane or diglyme, etc.; or a mixed solvent of these solvents, preferably a halogenated hydrocarbon.

A reaction temperature may vary depending on starting compounds, a reagent or a solvent, etc., and is generally 0° C. to 100° C., preferably 0° C. to 50° C.

A reaction time may vary depending on a reaction temperature, and is generally 1 hour to 48 hours, preferably 1 hour to 24 hours.

The twenty-first step is a step of preparing Compound (6) by treating Compound (18) with an acid in an organic solvent.

As the acid to be used, there may be mentioned, for example, an inorganic acid such as hydrochloric acid, hydrobromic acid, hydroiodic acid, sulfuric acid or nitric acid, etc.; or an organic sulfonic acid such as methanesulfonic acid, benzenesulfonic acid, p-toluenesulfonic acid, naphthalenesulfonic acid or camphorsulfonic acid, etc., preferably an organic sulfonic acid, particularly preferably p-toluenesulfonic acid. An amount of the acid to be used is generally 1 to 10-fold mol, preferably 1 to 5-fold mol based on an amount of Compound (18).

As the organic solvent to be used, it is not particularly limited so long as it does not inhibit the reaction, and dissolves the starting materials with a certain extent, and there may be mentioned, for example, an alcohol such as methanol, ethanol, propanol, butanol or ethylene glycol, etc.; an ether such as tetrahydrofuran, diethyl ether, diisopropyl ether, 1,4-dioxane or diglyme, etc.; an amide such as N,N-dimethylform-amide, N,N-dimethylacetamide or N-methyl-2-pyrrolidone, etc.; a sulfoxide such as dimethylsulfoxide, etc.; or a mixed solvent of these solvents, preferably an alcohol.

A reaction temperature may vary depending on starting compounds, a reagent or a solvent, etc., and is generally 0° C. to 100° C., preferably 0° C. to 50° C.

A reaction time may vary depending on a reaction temperature, and is generally 1 hour to 24 hours, preferably 1 hour to 12 hours.

The twenty-second step is a step of preparing Compound (7) by treating Compound (6) with methanesulfonyl chloride in the presence of a base in an organic solvent. The present step can be carried out in the same manner as in the above-mentioned "fourth step" except for using Compound (6) in place of Compound (1).

Compound (III) of the present invention can be prepared in the same manner as in Compound (I) of the present invention in accordance with the method described in the above-mentioned "Method 1" to "Method 3" using an optical isomer ((S)-isomer) (see WO 98/14192A or WO 2004/089890A) of Compound (2) in place of using a racemic mixture thereof. Also, Compound (III) of the present invention which is a desired optical isomer can be prepared by optically resolving the racemic mixture compound of Compound (I) of the present invention, or optically resolving its preparation intermediates (for example, Compounds (4), (5), (8) and (9)) and derived therefrom. As a method of optical resolution, it can be carried out by optionally selecting a usual method, for example, a column chromatography method using an optical resolution column, a preferential crystallization method, and a method of resolving with a diastereomer salt.

The desired compound formed by the above-mentioned respective reactions can be obtained from a reaction mixture according to the conventional manner. For example, it can be obtained by optionally neutralizing the reaction mixture, and when insoluble materials exist, after removing them by filtration, adding an organic solvent which does not miscible with water such as ethyl acetate, etc., after washing with water, separating an organic layer containing the desired compound, drying over a desiccant such as anhydrous magnesium sulfate, etc., and then removing a solvent.

The obtained desired compound can be separated and purified, if necessary, by a conventional method, for example, recrystallization; reprecipitation; or usually employed methods for separation and purification of an organic compound (for example, adsorption column chromatography method using a carrier such as silica gel, alumina, etc.; ion exchange chromatography method; or normal phase•reverse phase column chromatography method using silica gel or alkylated silica gel (preferably it is a high performance liquid chromatography.)) in an optional combination, eluting with an appropriate eluent.

The benzazepinone compound represented by the formula (I) of the present invention can exist as a hydrate or a solvate, and they are also included in the present invention.

Compound (I) of the present invention can be converted into a pharmaceutically acceptable addition salt according to the conventional manner, depending on necessity, and it can be directly separated as an addition salt from the reaction mixture.

As the pharmaceutically acceptable addition salt, there may be mentioned, for example, an inorganic acid addition salt such as hydrochloride, hydrobromide, hydroiodide, nitrate, sulfate or phosphate, etc.; or an organic acid addition salt such as acetate, trifluoroacetate, benzoate, oxalate, malonate, succinate, maleate, fumarate, tartrate, citrate, methanesulfonate, ethanesulfonate, trifluoromethanesulfonate, benzenesulfonate, p-toluenesulfonic acid, glutamate or aspartate, etc., preferably hydrochloride or trifluoroacetate.

Since the compound represented by the formula (I) of the present invention is a potent antagonist of an αv integrin receptor (particularly, $\alpha v\beta 3$, $\alpha v\beta 5$ and $\alpha v\beta 6$), so that it is useful as a therapeutic agent and/or a prophylactic agent of a disease to which an αv integrin receptor relates, for example, osteoporosis, vascular restenosis, angiogenesis, atherosclerosis, inflammatory arthritis, rheumatoid arthritis, cancer, metastatic tumor growth and fibrosis, and other diseases to which an αv integrin receptor relates.

When Compound (I) or a pharmaceutically acceptable salt thereof of the present invention is to be used as a therapeutic agent or a prophylactic agent of the above-mentioned diseases, it can be administered orally as such (as a starting powder itself) or by mixing with a suitable pharmaceutically acceptable excipient, diluent, etc., in the form of a tablet, capsule, granule, powder or syrup, etc., or non-orally administered by an injection or suppository, etc. (preferably orally).

These preparations can be prepared by using an additive such as an excipient (for example, a sugar derivative such as lactose, sucrose, glucose, mannitol or sorbitol, etc.; a starch derivative such as corn starch, potato starch, α-starch, dextrin or carboxymethyl starch, etc.; a cellulose derivative such as crystalline cellulose, low-substitution degree hydroxypropyl cellulose, hydroxypropylmethyl cellulose, carboxymethyl cellulose, calcium carboxymethyl cellulose or internally cross-linked sodium carboxymethyl cellulose, etc.; Gum Arabic; dextran; pulluran; a silicate derivative such as light silicic anhydride, synthetic aluminum silicate, calcium silicate or magnesium metasilicate aluminate, etc.; a phosphate derivative such as calcium hydrogen phosphate, etc.; a carbonate derivative such as calcium carbonate, etc.; or a sulfate derivative such as calcium sulfate, etc.), a binder (for example, the above-mentioned excipient; gelatin; polyvinylpyrrolidone; or polyethylene glycol, etc.), a disintegrant (for example, the above-mentioned excipient; a chemically modified starch or cellulose derivative such as croscarmellose sodium or carboxymethyl starch, etc.; or cross-linked polyvinylpyrrolidone, etc.), a lubricant (for example, talc; stearic acid; a stearic acid metal salt such as calcium stearate or magnesium stearate, etc.; colloidal silica; wax such as bee gum, candelilla wax, etc.; boric acid; glycol; D,L-leucine; a carboxylic acid such as fumaric acid or adipic acid, etc.; a sodium carboxlate such as sodium benzoate, etc.; a sulfate such as sodium sulfate, etc.; a lauryl sulfate such as sodium lauryl sulfate or magnesium lauryl sulfate, etc.; a sulfate such as sodium sulfate, etc.; a silicic acid such as silicic anhydride, silicic acid hydrate, etc.; or a starch derivative in the above-mentioned excipient, etc.), a stabilizer (for example, a paraoxybenzoic acid ester such as methylparaben or propylparaben, etc.); an alcohol such as chloro-butanol, benzyl alcohol or phenylethyl alcohol, etc.; benzalkonium chloride; a phenol such as phenol or cresol, etc.; thimerosal; acetic anhydride; or sorbic acid), a corrigent (for example, a conventionally used sweetening, souring, or flavoring agent, etc.), a diluent (for example, water, ethanol, propylene glycol, ethoxidized isostearyl alcohol or polyoxyethylene sorbitan fatty acid ester, etc.), a solvent for injection (for example, water, ethanol or glycerine, etc.), etc., in the conventional manner.

A dose of Compound (I) or a pharmaceutically acceptable salt thereof of the present invention may vary depending on symptom, an age, a body weight, etc., of a patient, and in the case of an oral administration, each can be administered with a lower limit of 0.01 mg/Kg (preferably 0.05 mg/Kg), and an upper limit of 500 mg/Kg (preferably 50 mg/Kg) per one time, and in the case of a non-oral administration, each can be administered with a lower limit of 0.001 mg/Kg (preferably 0.005 mg/Kg), and an upper limit of 50 mg/Kg (preferably 5 mg/Kg) per one time, with 1 to 6 times per day per an adult depending on symptom.

EXAMPLES

In the following, the present invention is explained in more detail by referring to Example, Reference example, and Test example, but the scope of the present invention is not limited by these.

Example 1

Ethyl 3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate hydrochloride 1-(a) 1-Bromo-4-hydroxy-2-butanone To 1.9 L of a methanol solution containing 169 g (1.92 mol) of 4-hydroxy-2-butanone was added dropwise 300 g (1.88 mol) of bromine at −5° C. over 30 minutes. After completion of the dropwise addition, the mixture was gradually elevated to room temperature, and stirred for 2 hours. Subsequently, 3.84 L (3.84 mol) of 2N sulfuric acid was added to the mixture at 0° C., and the resulting mixture was stirred at 10° C. for 3.5 hours, and further at room temperature for 22 hours.

After completion of the reaction, 325 g of sodium chloride was added to the reaction mixture, and the mixture was extracted with 5.4 L of a chloroform:methanol=2:1 (V/V) mixed solution. Moreover, the aqueous layer was extracted 4 times with 1.7 L of a chloroform:methanol=9:1 (V/V) mixed solution. The combined organic layers were washed with saturated aqueous sodium hydrogen carbonate solution, and then with a saturated aqueous sodium chloride solution, and concentrated under reduced pressure to obtain 215 g (pure content 176 g) of the title compound as a pale brown oily product.

(Yield 55%)

Mass spectrum (CI, m/z): 167 ($M^+$).

$^1$H-NMR spectrum (CDCl$_3$, δ ppm): 2.14 (t, J=6.4 Hz, 1H), 2.93 (t, J=5.5 Hz, 2H), 3.89-3.95 (m, 4H).

1-(b) 2-(Imidazo[1,2-a]pyrimidin-2-yl)ethanol

To 4.4 L of an ethanol solution containing 420 g (pure content 351 g, 2.10 mol) of 1-bromo-4-hydroxy-2-butanone obtained in the same reaction as in Example 1-(a) was added 210 g (2.21 mol) of 2-aminopyrimidine, and the mixture was refluxed for 20 hours.

After completion of the reaction, to the reaction mixture was added 3 L of a supernatant of an aqueous solution obtained by adding 392 g (2.84 mol) of potassium carbonate and 565 g of sodium chloride to 4 L of water, and then, the resultant mixture was extracted with 7 L of chloroform. Moreover, the aqueous layer was extracted 3 times with 3 L of a mixed solution comprising chloroform:methanol=3:1 (V/V). After drying the combined organic layers over anhydrous sodium sulfate, it was concentrated under reduced pressure. The obtained residue was applied to silica gel column chromatography (eluent; ethyl acetate→ethyl acetate:ethanol:28% aqueous ammonia:water=70:25:2.5:2.5 (V/V/V/V)), and the separated fractions containing the desired product were concentrated under reduced pressure to obtain 104 g of the title compound as pale brown solid. (Yield 30%)

Mass spectrum (CI, m/z): 164 ($M^+$+1).

$^1$H-NMR spectrum (DMSO-d$_6$, δ ppm): 2.86 (td, $J_1$=6.8 Hz, $J_2$=0.5 Hz, 2H), 3.74 (t, J=6.8 Hz, 2H), 4.68 (s, 1H), 7.00 (dd, $J_1$=6.7 Hz, $J_2$=4.2 Hz, 1H), 7.71 (s, 1H), 8.46 (dd, $J_1$=4.2 Hz, $J_2$=2.0 Hz, 1H), 8.90 (dd, $J_1$=6.7 Hz, $J_2$=2.0 Hz, 1H).

1-(c) Ethyl 8-[2-(imidazo[1,2-a]pyrimidin-2-yl)ethoxy]-3-oxo-2-(2,2,2-trifluoroethyl)-2,3,4,5-tetrahydro-1H-2-benzazepin-4-acetate To 55 mL of a tetrahydrofuran solution containing 0.39 g (2.40 mmol) of 2-(imidazo[1,2-a]pyrimidin-2-yl)ethanol obtained in Example 1-(b) were added 0.69 g (2.00 mmol) of ethyl 8-hydroxy-3-oxo-2-(2,2,2-trifluoroethyl)-2,3,4,5-tetrahydro-1H-2-benzazepin-4-acetate (see WO 98/14192 A) and 0.74 g (2.80 mmol) of triphenyl-phosphine, and the mixture was stirred under ice-cooling. Then, 2.6 mL of a tetrahydrofuran solution containing 0.53 g (2.60 mmol) of diisopropyl azodicarboxylate was added dropwise to the mixture over 3 minutes, the mixture was gradually elevated to room temperature, and stirred for 14 hours.

After completion of the reaction, the reaction mixture was concentrated under reduced pressure, the residue was applied to silica gel column chromatography (eluent; chloroform:tetrahydrofuran:methanol=18:1:1 (V/V/V)). The separated fractions containing the desired product were concentrated under reduced pressure to obtain 0.31 g of the title compound as a colorless oily product. (Yield 32%)

Mass spectrum (CI, m/z): 491 ($M^+$+1).

$^1$H-NMR spectrum (CDCl$_3$, δ ppm): 1.26 (t, J=7.1 Hz, 3H), 2.44 (dd, $J_1$=16.8 Hz, $J_2$=5.4 Hz, 1H), 2.83-3.03 (m, 3H), 3.30 (t, J=6.6 Hz, 2H), 3.75-3.92 (m, 1H), 3.92-4.03 (m, 1H), 3.96 (d, J=16.6 Hz, 1H), 4.10-4.21 (m, 1H), 4.16 (q, J=7.1 Hz, 2H), 4.39 (td, $J_1$=6.6 Hz, $J_2$=1.3 Hz, 2H), 5.32 (d, J=16.6 Hz, 1H), 6.65 (d, J=2.7 Hz, 1H), 6.80-6.85 (m, 2H), 7.01 (d, J=8.5 Hz, 1H), 7.43 (s, 1H), 8.36 (dd, $J_1$=6.7 Hz, $J_2$=2.1 Hz, 1H), 8.51 (dd, $J_1$=4.0 Hz, $J_2$=2.1 Hz, 1H).

1-(d) Ethyl 3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate hydrochloride To 11 mL of an ethanol solution containing 0.28 g (0.57 mmol) of ethyl 8-[2-(imidazo[1,2-a]pyrimidin-2-yl)ethoxy]-3-oxo-2-(2,2,2-trifluoroethyl)-2,3,4,5-tetra-hydro-1H-2-benzazepin-4-acetate obtained in Example 1-(c) were added 5.5 mL of 3.2M hydrogen chloride/ethanol solution and 0.14 g of 10% palladium carbon, and the mixture was stirred under hydrogen atmosphere at room temperature for 1 hour.

After completion of the reaction, the reaction mixture was filtered with Celite (Trade name), the residue was washed with ethanol and the obtained filtrate was concentrated under reduced pressure to obtain 0.28 g of the title compound as pale yellow foam. (Yield 93%)

Mass spectrum (FAB, m/z): 495 ($M^+$+1).

$^1$H-NMR spectrum (DMSO-$d_6$, δ ppm): 1.17 (t, J=7.1 Hz, 3H), 1.96-2.00 (m, 2H), 2.63-2.76 (m, 2H), 2.89 (t, J=6.3 Hz, 2H), 3.01 (dd, $J_1$=17.0 Hz, $J_2$=4.0 Hz, 1H), 3.78-3.89 (m, 1H), 3.87 (t, J=5.7 Hz, 2H), 4.04 (q, J=7.1 Hz, 2H), 4.11-4.29 (m, 5H), 5.31 (d, J=16.4 Hz, 1H), 6.80-6.85 (m, 3H), 7.04 (d, J=9.3 Hz, 1H), 8.23 (brs, 1H), 12.29 (brs, 1H).

Example 2

3-oxo-8-[2-(5,6,7,8-tetrahydroimidazo[1,2-a]pyrimidin-2-yl)ethoxy]-2-(2,2,2-tri-fluoroethyl)-2,3,4,5-tetrahydro-1H-2-benzazepin-4-acetic acid trifluoroacetate In 2 mL of a mixed solution comprising methanol: tetrahydrofuran=1:1 was dissolved 0.054 g (0.10 mmol) of ethyl 3-oxo-8-[2-(5,6,7,8-tetrahydroimidazo[1,2-a]-pyrimidin-2-yl)ethoxy]-2-(2,2,2-trifluoroethyl)-2,3,4,5-tetrahydro-1H-2-benzazepin-4-acetate hydrochloride obtained in Example 1-(d), 0.2 mL of water and 0.3 mL of 1N sodium hydroxide aqueous solution were added to the solution under ice-cooling, and the mixture was stirred at room temperature for 2 hours.

After completion of the reaction, 0.025 mL of acetic acid was added to the reaction mixture, and the mixture was concentrated under reduced pressure. The obtained residue was purified by solid phase extraction (cartridge; Sep-Pak C18 (5 g/20 mL (manufactured by Waters Co.), eluent; 0.05% trifluoroacetic acid aqueous solution→acetonitrile:0.05% trifluoroacetic acid aqueous solution=3:7 (V/V)) to obtain 31.6 mg of the title compound as pale yellow foam. (Yield 54%)

Mass spectrum (FAB, m/z): 467 ($M^+$+1).

$^1$H-NMR spectrum (DMSO-$d_6$, δ ppm): 1.96-2.00 (m, 2H), 2.40 (dd, $J_1$=17.2 Hz, $J_2$=5.1 Hz, 1H), 2.62-2.72 (m, 2H), 2.89 (t, J=6.2 Hz, 2H), 3.01 (dd, $J_1$=17.2 Hz, $J_2$=3.8 Hz, 1H), 3.73-3.78 (m, 1H), 3.87 (t, J=5.7 Hz, 2H), 4.03-4.30 (m, 5H), 5.32 (d, J=16.1 Hz, 1H), 6.57-6.84 (m, 3H), 7.04 (d, J=8.3 Hz, 1H), 8.18 (brs, 1H), 12.16 (brs, 2H).

Example 3

3-Oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetic acid trifluoroacetate 3-(a) 2-amidazo[1,2-b][1,2,4]triazin-6-yl)ethanol To 40 mL of an ethanol solution containing 1.92 g (20.0 mmol) of 3-amino-1,2,4-triazine was added 3.67 g (22.0 mmol) of 1-bromo-4-hydroxy-2-butanone obtained in Example 1-(a), and the mixture was refluxed for 2 hours.

After completion of the reaction, the reaction mixture was concentrated under reduced pressure, to the obtained residue was added 200 mL of a mixed solution comprising chloroform:methanol=9:1 (V/V), and insoluble materials were filtered off. The filtrate was successively washed with water and a saturated aqueous sodium chloride solution, dried over anhydrous sodium sulfate, and concentrated under reduced pressure. The obtained residue was applied to silica gel column chromatography (eluent; chloroform:methanol=30:1→9:1 (V/V)), and the separated fractions containing the desired product were concentrated under reduced pressure to obtain 0.24 g of the title compound as yellow solid. (Yield 7%)

Mass spectrum (CI, m/z): 165 ($M^+$+1).

$^1$H-NMR spectrum (CDCl$_3$, δ ppm): 3.13 (td, $J_1$=5.5 Hz, $J_2$=0.5 Hz, 2H), 4.09 (t, J=5.5 Hz, 2H), 7.85 (s, 1H), 8.33 (d, J=1.9 Hz, 1H), 8.40 (d, J=1.9 Hz, 1H).

3-(b) Ethyl 8-[2-(imidazo[1,2-b][1,2,4]triazin-6-yl)ethoxy]-3-oxo-2-(2,2,2-trifluoro-ethyl)-2,3,4,5-tetrahydro-1H-2-benzazepin-4-acetate To 50 mL of a tetrahydrofuran solution containing 0.81 g (4.94 mmol) of 2-(imidazo[1,2-b][1,2,4]triazin-6-yl)ethanol obtained in the same reaction as in Example 3-(a) were added 1.66 g (4.80 mmol) of ethyl 8-hydroxy-3-oxo-2-(2,2,2-trifluoroethyl)-2,3,4,5-tetrahydro-1H-2-benzazepin-4-acetate (see WO 98/14192A) and 1.76 g (6.71 mmol) of triphenylphosphine, and the mixture was stirred under ice-cooling. Then, 9 mL of a tetrahydrofuran solution containing 1.26 g (6.23 mmol) of diisopropyl azodicarboxylate was added dropwise to the mixture over 45 minutes, the mixture was gradually elevated to room temperature, and stirred for 12 hours.

After completion of the reaction, the reaction mixture was concentrated under reduced pressure, and the residue was applied to silica gel column chromatography (eluent; chloroform:tetrahydrofuran=9:1 (V/V)). The separated fractions containing the desired product were concentrated under reduced pressure to obtain 0.77 g of the title compound as yellow foam. (Yield 33%)

Mass spectrum (CI, m/z): 492 ($M^+$+1).

$^1$H-NMR spectrum (CDCl$_3$, δ ppm): 1.26 (t, J=7.2 Hz, 3H), 2.44 (dd, $J_1$=16.8 Hz, $J_2$=5.4 Hz, 1H), 2.83-3.05 (m, 3H), 3.35-3.39 (m, 2H), 3.78-3.88 (m, 1H), 3.91-4.02 (m, 2H), 4.10-4.24 (m, 1H), 4.16 (q, J=7.2 Hz, 2H), 4.37-4.44 (m, 2H), 5.32 (d, J=16.8 Hz, 1H), 6.65 (d, J=2.7 Hz, 1H), 6.82 (dd, $J_1$=8.5 Hz, $J_2$=2.7 Hz, 1H), 7.02 (d, J=8.5 Hz, 1H), 7.90 (s, 1H), 8.31 (d, J=2.0 Hz, 1H), 8.40 (d, J=2.0 Hz, 1H).

3-(c) 8-[2-(Imidazo[1,2-b][1,2,4]triazin-6-yl)ethoxy]-3-oxo-2-(2,2,2-trifluoroethyl)-2,3,4,5-tetrahydro-1H-2-benzazepin-4-acetic acid To 1 mL of an ethanol solution containing 49.2 mg (0.100 mmol) of ethyl 8-[2-(imidazo[1,2-b][1,2,4]triazin-6-yl)ethoxy]-3-oxo-2-(2,2,2-trifluoroethyl)-2,3,4,5-tetr-ahydro-1H-2-benzazepin-4-acetate obtained in Example 3-(b) was added 200 μL (200 mmol) of 1N sodium hydroxide aqueous solution, and the mixture was stirred at room temperature for 20 hours.

After completion of the reaction, 1 mL of a saturated aqueous ammonium chloride solution was added to the reaction mixture, and the mixture was extracted with 30 mL of a mixed solution comprising chloroform:methanol=9:1 (VN). After drying the organic layer over anhydrous sodium sulfate, it was concentrated under reduced pressure. The obtained residue was applied to silica gel column chromatography (eluent; chloroform:methanol=25:1 (V/V)→chloroform:methanol:acetic acid=25:1:0.1 (V/V/V)), and the separated fractions containing the desired product were concentrated under reduced pressure to obtain 28.7 mg of the title compound as pale yellow solid.
(Yield 62%)
Mass spectrum (CI, m/z): 464 (M$^+$+1).
$^1$H-NMR spectrum (DMSO-d$_6$, δ ppm): 2.36 (dd, J$_1$=16.8 Hz, J$_2$=5.1 Hz, 1H), 2.59-2.73 (m, 2H), 2.97-3.03 (m, 1H), 3.24 (t, J=6.6 Hz, 2H), 3.71-3.82 (m, 1H), 4.13-4.25 (m, 3H), 4.35 (t, J=6.6 Hz, 2H), 5.30 (d, J=16.8 Hz, 1H), 6.81-6.85 (m, 2H), 7.01-7.04 (m, 1H), 8.27 (s, 1H), 8.53 (d, J=2.0 Hz, 1H), 8.63 (d, J=2.0 Hz, 1H).

3-(d) 3-oxo-8-[2-(1,2,3,4-tetrahydroimidazo[1,2-b] [1,2,4]triazin-6-yl)ethoxy]-2-(2,2,2-trifluoroethyl)-2, 3,4,5-tetrahydro-1H-2-benzazepin-4-acetic acid trifluoroacetate To 1.7 mL of an ethanol solution containing 26.4 mg (0.057 mmol) of 8-[2-(imidazo[1,2-b][1,2,4]triazin-6-yl)ethoxy]-3-oxo-2-(2,2,2-trifluoroethyl)-2,3,4,5-tetrahydro-1H-2-benzazepin-4-acetic acid obtained in Example 3-(c) was added 3.5 mg (0.093 mmol) of sodium borohydride, the mixture was stirred at room temperature for 1 hour, 2.5 mg (0.066 mmol) of sodium borohydride was further added to the same, and the resulting mixture was stirred at the same temperature for 1 hour.
After completion of the reaction, the reaction mixture was concentrated under reduced pressure, and the residue was purified by high performance liquid chromato-graphy (column; TSK-GEL ODS-80Ts (20 mm×250 mm (available from TOSOH CORPORATION), eluent; acetonitrile:water:trifluoroacetic acid=300:700:1 (V/V/V), flow rate; 20 mL/min) to obtain 8.9 mg of the title compound as white foam. (Yield 27%)
Mass spectrum (CI, m/z): 468 (M$^+$+1).
$^1$H-NMR spectrum (CD$_3$CN, δ ppm): 2.45 (dd, J$_1$=16.8 Hz, J$_2$=4.8 Hz, 1H), 2.72-2.82 (m, 2H), 2.87-2.92 (m, 2H), 2.99-3.06 (m, 1H), 3.18-3.25 (m, 2H), 3.37-3.41 (m, 2H), 3.74-3.85 (m, 1H), 4.01-4.22 (m, 5H), 5.30 (d, J=16.8 Hz, 1H), 6.50 (s, 1H), 6.80-6.85 (m, 2H), 7.04 (d, J=8.5 Hz, 1H), 8.96 (s, 1H), 13.62 (brs, 1H).

Example 4

(4S)-3-oxo-8-[2-(5,6,7,8-tetrahydroimidazo[1,2-a] pyrimidin-2-yl)ethoxy]-2-(2,2,2-trifluoroethyl)-2,3, 4,5-tetrahydro-1H-2-benzazepin-4-acetic acid 4-(a) 2-(2-tert-Butyldimethylsilyloxyethyl)-imidazo [1,2-a]pyrimidine To 300 mL of a dimethylformamide solution containing 60.0 g (368 mmol) of 2-(imidazo[1,2-a]pyrimidin-2-yl)ethanol obtained in Example 1-(b) were added 61.0 g (405 mmol) of tert-butyldimethylsilyl chloride and 55.1 g (810 mmol) of imidazole at room temperature, and the resulting mixture was stirred at the same temperature for 12 hours.
After completion of the reaction, the reaction mixture was poured into 500 mL of a saturated aqueous sodium hydrogen carbonate solution, and extracted twice with 800 mL of toluene. The combined organic layers were washed with a saturated aqueous sodium chloride solution, dried over anhydrous magnesium sulfate, and concentrated under reduced pressure to obtain 70.3 g of the title compound as pale brown solid. (Yield 69%)
Mass spectrum (CI, m/z): 278 (M$^+$+1).
$^1$H-NMR spectrum (CDCl$_3$, δ ppm): 0.03 (s, 6H), 0.88 (s, 9H), 3.05 (td, J$_1$=6.8 Hz, J$_2$=0.6 Hz, 2H), 4.01 (t, 2H), 6.81 (dd, J$_1$=6.6 Hz, J$_2$=4.2 Hz, 1H), 7.39 (s, 1H), 8.36 (dd, J$_1$=6.6 Hz, J$_2$=2.0 Hz, 1H), 8.49 (dd, J$_1$=4.2 Hz, J$_2$=2.0 Hz, 1H).

4-(b) tert-Butyl 2-(2-tert-butyldimethylsilyloxyethyl)-6,7-dihydro-5H-imidazo[1,2-a]-pyrimidine-8-carboxylate To 650 mL of a methanol solution containing 60.0 g (216 mmol) of 2-(2-tert-butyldimethylsilyloxyethyl)-imidazo[1, 2-a]pyrimidine obtained in Example 4-(a) was added 20.5 g (542 mmol) of sodium borohydride at room temperature, and the resulting mixture was stirred at the same temperature for 5 hours.
After completion of the reaction, the reaction mixture was concentrated under reduced pressure to a volume of 350 mL, and poured into 500 mL of water. The mixture was extracted twice with 500 mL of ethyl acetate, and the extracts were dried over anhydrous magnesium sulfate and concentrated under reduced pressure. The obtained residue was dissolved in 350 mL of dichloromethane, then, 35.6 mL (256 mmol) of triethylamine, 2.60 g (21.3 mmol) of 4-dimethylaminopyridine and 55.9 g (256 mmol) of di-tert-butyl dicarbonate were added to the mixture at room temperature, and the resulting mixture was stirred at the same temperature for 2 hours. After completion of the reaction, the reaction mixture was concentrated under reduced pressure, the residue was poured into 500 mL of a saturated aqueous sodium hydrogen carbonate solution, and extracted twice with 500 mL of ethyl acetate. The combined organic layers were washed with a saturated aqueous sodium chloride solution, dried over anhydrous magnesium sulfate, and concentrated under reduced pressure to obtain 80.2 g of the title compound as yellow oil. (Yield 97%)
Mass spectrum (CI, m/z): 381 (M$^+$).
$^1$H-NMR spectrum (CDCl$_3$, δ ppm): 0.04 (s, 6H), 0.89 (s, 9H), 1.54 (s, 9H), 2.03-2.11 (m, 2H), 2.78 (td, J$_1$=7.2 Hz, J$_2$=0.7 Hz, 2H), 3.80-3.90 (m, 6H), 6.43 (s, 1H).

4-(c) tert-Butyl 2-(2-hydroxyethyl)-6,7-dihydro-5H-imidazo[1,2-a]pyrimidine-8-carboxylate To 150 mL of a methanol solution containing 80.2 g (210 mmol) of tert-butyl 2-[2-(tert-butyldimethylsilyloxy)ethyl]-6,7-dihydro-5H-imidazo[1,2-a]pyrimidine-8-carboxylate obtained in Example 4-(b) was added 47.9 g (252 mmol) of p-toluene-sulfonic acid monohydrate at room temperature, and the resulting mixture was stirred at the same temperature for 3.5 hours.
After completion of the reaction, the reaction mixture was poured into 500 mL of a saturated aqueous sodium hydrogen carbonate solution, and the mixture was extracted eight times with 300 mL of ethyl acetate, and then, twice with 200 mL of a mixed solution comprising chloroform/methanol=4:1 (V/V). After drying the combined organic layers over anhydrous sodium sulfate, it was concentrated under reduced pressure to obtain 58.0 g of the title compound as yellow solid. (Yield: quantitative)
Mass spectrum (CI, m/z): 267 (M$^+$).
$^1$H-NMR spectrum (CDCl$_3$, δ ppm): 1.56 (s, 9H), 2.08-2.16 (m, 2H), 2.36 (s, 1H), 2.72 (td, J$_1$=5.4 Hz, J$_2$=0.7 Hz, 2H), 3.84-3.93 (m, 6H), 6.44 (s, 1H).

4-(d) tert-Butyl 2-(2-methanesulfonyloxyethyl)-6,7-dihydro-5H-imidazo[1,2-a]-pyrimidine-8-carboxylate To 150 mL of a dichloromethane solution containing 20.0 g (74.8 mmol) of tert-butyl 2-(2-hydroxyethyl)-6,7-dihydro- 5H-imidazo[1,2-a]pyrimidine-8-carboxylate obtained in Example 4-(c) were added 11.5 mL (82.3 mmol) of triethylamine and 6.37 mL (82.3 mmol) of methanesulfonyl chloride at room temperature, and the resulting mixture was stirred at the same temperature for 2 hours.

After completion of the reaction, the reaction mixture was poured into 500 mL of a saturated aqueous sodium hydrogen carbonate solution, and the mixture was extracted twice with 300 mL of ethyl acetate. The combined organic layers were dried over anhydrous magnesium sulfate and concentrated under reduced pressure to obtain 20.6 g of the title compound as brown oil. (Yield 80%)

Mass spectrum (CI, m/z): 345 ($M^+$).

$^1$H-NMR spectrum (CDCl$_3$, δ ppm): 1.55 (s, 9H), 2.06-2.14 (m, 2H), 2.97 (s, 3H), 3.01 (td, $J_1$=6.7 Hz, $J_2$=0.5 Hz, 2H), 3.82-3.86 (m, 2H), 3.91 (t, J=6.2 Hz, 2H), 4.48 (t, J=6.7 Hz, 2H), 6.52 (s, 1H).

4-(e) Ethyl(4S)-3-oxo-8-[2-(8-tert-butoxycarbonyl-5,6,7,8-tetrahydroimidazo[1,2-a]-pyrimidin-2-yl)ethoxy]-2-(2,2,2-trifluoroethyl)-2,3,4,5-tetrahydro-1H-2-benzazepin-4-acetate To 40 mL of a tetrahydrofuran solution containing 3.87 g (11.2 mmol) of ethyl (4S)-8-hydroxy-3-oxo-2-(2,2,2-trifluoroethyl)-2,3,4,5-tetrahydro-1H-2-benzazepin-4-acetate (see WO 2004/089890A) was added 469 mg (11.7 mmol) of sodium hydride (mineral oil 60% dispersed material) at room temperature, and the resulting mixture was stirred for 30 minutes. Then, 10 mL of a tetrahydrofuran solution containing 3.54 g (10.2 mmol) of tert-butyl 2-(2-methanesulfonyloxyethyl)-6,7-dihydro-5H-imidazo[1,2-a]pyrimidine-8-carboxylate obtained in Example 4-(d) was added to the mixture at room temperature, and the resulting mixture was stirred at the same temperature for 20 hours.

After completion of the reaction, the reaction mixture was poured into 200 mL of water, and the mixture was extracted twice with 100 mL of ethyl acetate. The combined organic layers were dried over anhydrous magnesium sulfate, and concentrated under reduced pressure. The obtained residue was applied to silica gel column chromatography (eluent; ethyl acetate→chloroform:methanol=14:1 (V/V)), and the separated fractions containing the desired product were concentrated under reduced pressure to obtain 4.60 g of the title compound as pale brown foam. (Yield 76%)

Mass spectrum (CI, m/z): 595 ($M^+$+1).

$^1$H-NMR spectrum (CDCl$_3$, δ ppm): 1.27 (t, J=7.2 Hz, 3H), 1.54 (s, 9H), 2.05-2.13 (m, 2H), 2.44 (dd, $J_1$=16.8 Hz, $J_2$=5.6 Hz, 1H), 2.87-3.05 (m, 5H), 3.82-3.99 (m, 7H), 4.11-4.24 (m, 5H), 5.33 (d, J=16.8 Hz, 1H), 6.50 (s, 1H), 6.64 (d, J=2.4 Hz, 1H), 6.80 (dd, $J_1$=8.5 Hz, $J_2$=2.7 Hz, 1H), 7.00 (d, J=8.5 Hz, 1H).

4-(f) Ethyl(4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate hydrochloride To 8 mL of a tetrahydrofuran solution containing 4.60 g (7.74 mmol) of ethyl (4S)-3-oxo-8-[2-(8-tert-butoxycarbonyl-5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate obtained in Example 4-(e) were added 8 mL of acetic acid and 24 mL of water, the resulting mixture was stirred at 70° C. for 7 hours.

After completion of the reaction, the reaction mixture was concentrated under reduced pressure, and the residue was applied to silica gel column chromatography (eluent; chloroform:methanol:acetic acid=90:10:3 (V/V/V)). The separated fractions containing the desired product were concentrated under reduced pressure, the obtained oil was dissolved in 4 mL of ethanol, and after adding 8.6 mL of 2.7N hydrogen chloride/ethanol solution, the mixture was concentrated under reduced pressure to obtain 3.10 g of the title compound as pale yellow foam. (Yield 75%)

Mass spectrum (FAB, m/z): 495 ($M^+$+1).

$^1$H-NMR spectrum (DMSO-d$_6$, δ ppm): 1.17 (t, J=7.1 Hz, 3H), 1.94-2.02 (m, 2H), 2.63-2.76 (m, 2H), 2.89 (t, J=6.2 Hz, 2H), 3.01 (dd, $J_1$=17.5 Hz, $J_2$=3.9 Hz, 1H), 3.78-3.89 (m, 3H), 4.04 (q, J=7.1 Hz, 2H), 4.11-4.29 (m, 5H), 5.32 (d, J=16.6 Hz, 1H), 6.81-6.85 (m, 3H), 7.05 (d, J=9.3 Hz, 1H), 8.23 (brs, 1H), 12.28 (brs, 1H).

4-(g) (4S)-3-Oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetic acid In 1.0 mL of a mixed solution comprising tetrahydrofuran/ethanol=1:1 (V/V) was dissolved 100 mg (0.188 mmol) of ethyl(4S)-3-oxo-8-[2-(5,6,7,8-tetrahydro-imidazo[1,2-a]pyrimidin-2-yl)ethoxy]-2-(2,2,2-trifluoroethyl)-2,3,4,5-tetrahydro-1H-2-benzazepin-4-acetate hydrochloride obtained in Example 4-(f), 1.13 mL (1.13 mmol) of 1N sodium hydroxide aqueous solution was added to the solution, and the resulting mixture was stirred at 0° C. for 10 hours.

After completion of the reaction, 75 μL (1.32 mmol) of acetic acid was added to the reaction mixture, an inorganic salt was removed by Sep-Pak (tradename), and then, it was concentrated under reduced pressure. The obtained residue was applied to silica gel column chromatography (eluent; chloroform:methanol:acetic acid=90:10:6 (V/V/V)), and the separated fractions containing the desired product were concentrated under reduced pressure to obtain 67.2 mg of the title compound as white solid. (Yield 77%)

Mass spectrum (FAB, m/z): 467 ($M^+$+1).

$^1$H-NMR spectrum (CDCl$_3$, δ ppm): 2.06-2.12 (m, 3H), 2.41 (dd, $J_1$=15.5 Hz, $J_2$=8.2 Hz, 1H), 2.78-2.95 (m, 4H), 3.10 (dd, $J_1$=17.6 Hz, $J_2$=4.4 Hz, 1H), 3.44 (t, J=5.4 Hz, 2H), 3.74-3.85 (m, 5H), 4.13-4.27 (m, 3H), 5.16 (d, J=16.6 Hz, 1H), 6.20 (s, 1H), 6.54 (d, J=2.4 Hz, 1H), 6.76 (dd, $J_1$=8.5 Hz, $J_2$=2.7 Hz, 1H), 6.86 (d, J=8.5 Hz, 1H).

Example 5

Propyl(4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate hydrochloride 5-(a) (4S)-3-oxo-8-[2-(8-tert-butoxycarbonyl-5,6,7,8-tetrahydroimidazo[1,2-a]-pyrimidin-2-yl)ethoxy]-2-(2,2,2-trifluoroethyl)-2,3,4,5-tetrahydro-1H-2-benzazepin-4-acetic acid In 20 mL of a methyl tert-butyl ether solution was dissolved 7.00 g (11.8 mmol) of ethyl(4S)-3-oxo-8-[2-(8-tert-butoxycarbonyl-5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate obtained in the same manner as in Example 4-(e), 10 mL of purified water and 1.04 g (24.8 mmol) of lithium hydroxide monohydrate were added to the solution and the resulting mixture was stirred at 50° C. for 3 hours.

After completion of the reaction, 100 mL of purified water and 50 mL of methyl tert-butyl ether were added to the reaction mixture, and the aqueous layer was separated. To the obtained aqueous layer was added 1N hydrogen chloride aqueous solution to adjust a pH thereof to 5.0, and the mixture was extracted with 500 mL of a mixed solution comprising chloroform:methanol=8:2 (V/V). The organic layer was washed with a saturated aqueous sodium chloride solution, dried over anhydrous sodium sulfate, and concentrated under reduced pressure to obtain 7.25 g of the title compound as pale yellow foam. (Yield: quantitative)

Mass spectrum (FAB, m/z): 567 ($M^+$+1).

$^1$H-NMR spectrum (DMSO-$d_6$, δ ppm): 1.47 (s, 9H), 1.97-2.04 (m, 2H), 2.39 (dd, $J_1$=16.8 Hz, $J_2$=4.9 Hz, 1H), 2.61-2.72 (m, 2H), 2.85 (t, J=6.7 Hz, 2H), 3.00 (dd, $J_1$=17.6 Hz, $J_2$=3.7 Hz, 1H), 3.72-3.92 (m, 5H), 4.10-4.28 (m, 5H), 5.30 (d, J=16.6 Hz, 1H), 6.75-6.83 (m, 3H), 7.01-7.05 (m, 1H), 12.15 (brs, 1H).

5-(b) Propyl(4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate hydrochloride 703 mg (1.24 mmol) of (4S)-3-oxo-8-[2-(8-tert-butoxycarbonyl-5,6,7,8-tetra-hydroimidazo[1,2-a]pyrimidin-2-yl)ethoxy]-2-(2,2,2-trifluoro ethyl)-2,3,4,5-tetrahydro-1H-2-benzazepin-4-acetic acid obtained in Example 5-(a) and 1.86 mL (24.8 mmol) of 1-propyl alcohol were mixed, 12.4 mL (49.6 mmol) of 4N hydrogen chloride/1,4-dioxane solution was added to the mixture, and the resulting mixture was stirred under nitrogen gas atmosphere at 45° C. for 4.5 hours.

After completion of the reaction, the reaction mixture was concentrated under reduced pressure, the residue was applied to silica gel column chromatography (eluent; ethyl acetate→chloroform:methanol=19:1 (V/V)), and the separated fractions containing the desired product were concentrated under reduced pressure to obtain 533 mg of the title compound as pale yellow foam. (Yield 79%)

Mass spectrum (FAB, m/z): 509 ($M^+$+1)

$^1$H-NMR spectrum (DMSO-$d_6$, δ ppm): 0.88 (t, J=7.4 Hz, 3H), 1.51-1.63 (m, 2H), 1.94-2.01 (m, 2H), 2.63-2.77 (m, 2H), 2.89 (t, J=6.2 Hz, 2H), 3.01 (dd, $J_1$=17.8 Hz, $J_2$=4.2 Hz, 1H), 3.79-3.89 (m, 3H), 3.96 (t, J=6.6 Hz, 2H), 4.10-4.29 (m, 5H), 5.31 (d, J=16.4 Hz, 1H), 6.80-6.85 (m, 3H), 7.04 (d, J=9.3 Hz, 1H), 8.18 (brs, 1H), 12.24 (brs, 1H).

Example 6

Isopropyl(4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate hydrochloride 640 mg (1.13 mmol) of (4S)-3-oxo-8-[2-(8-tert-butoxycarbonyl-5,6,7,8-tetrahydroimidazo[1,2-a]pyrimidin-2-yl)ethoxy]-2-(2,2,2-trifluoro ethyl)-2,3,4,5-tetrahydro-1H-2-benzazepin-4-acetic acid obtained in Example 5-(a) and 2.00 mL (26.1 mmol) of 2-propyl alcohol were mixed, 11.3 mL (45.2 mmol) of 4N hydrogen chloride/1,4-dioxane solution was added to the mixture, and the resulting mixture was stirred under nitrogen gas atmosphere at 45° C. for 4.5 hours.

After completion of the reaction, the reaction mixture was concentrated under reduced pressure, the residue was applied to silica gel column chromatography (eluent; chloroform:methanol=19:1 (V/V)), and the separated fractions containing the desired product were concentrated under reduced pressure to obtain 424 mg of the title compound as pale yellow foam. (Yield 69%)

Mass spectrum (FAB, m/z): 509 ($M^+$+1)

$^1$H-NMR spectrum (DMSO-$d_6$, δ ppm): 1.16 (d, J=6.2 Hz, 3H), 1.17 (d, J=6.2 Hz, 3H), 1.94-2.01 (m, 2H), 2.63-2.72 (m, 2H), 2.89 (t, J=6.3, 2H), 3.00 (dd, $J_1$=17.7 Hz, $J_2$=4.0 Hz, 1H), 3.76-3.89 (m, 3H), 4.11-4.26 (m, 5H), 4.86 (septet, J=6.2 Hz, 1H), 5.31 (d, J=16.4 Hz, 1H), 6.80-6.85 (m, 3H), 7.04 (d, J=9.3 Hz, 1H), 8.19 (brs, 1H), 12.26 (brs, 1H).

Example 7

Heptyl(4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate hydrochloride 70.0 mg (0.124 mmol) of (4S)-3-oxo-8-[2-(8-tert-butoxycarbonyl-5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetic acid obtained in Example 5-(a) and 88 µL (0.62 mmol) of heptyl alcohol were mixed, 1.55 mL (6.20 mmol) of 4N hydrogen chloride/1,4-dioxane solution was added to the mixture, and the resulting mixture was stirred under nitrogen gas atmosphere at 50° C. for 4 hours.

After completion of the reaction, the reaction mixture was concentrated under reduced pressure, the residue was applied to silica gel column chromatography (eluent; ethyl acetate→chloroform:methanol=14:1 (V/V)), and the separated fractions containing the desired product were concentrated under reduced pressure to obtain 58.2 mg of the title compound as pale yellow foam. (Yield 78%)

Mass spectrum (FAB, m/z): 565 ($M^+$+1).

$^1$H-NMR spectrum (DMSO-$d_6$, δ ppm): 0.86 (t, J=6.8 Hz, 3H), 1.24-1.28 (m, 8H), 1.52-1.57 (m, 2H), 1.94-2.01 (m, 2H), 2.63-2.76 (m, 2H), 2.89 (t, J=6.2 Hz, 2H), 3.01 (dd, $J_1$=17.1 Hz, $J_2$=3.9 Hz, 1H), 3.77-3.89 (m, 3H), 3.99 (t, J=6.6 Hz, 2H), 4.11-4.28 (m, 5H), 5.31 (d, J=16.4 Hz, 1H), 6.80-6.85 (m, 3H), 7.04 (d, J=9.3 Hz, 1H), 8.25 (brs, 1H), 12.33 (brs, 1H).

Example 8

Undecyl(4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate hydrochloride 704 mg (1.24 mmol) of (4S)-3-oxo-8-[2-(8-tert-butoxycarbonyl-5,6,7,8-tetra-hydroimidazo[1,2-a]pyrimidin-2-yl)ethoxy]-2-(2,2,2-trifluoroethyl)-2,3,4,5-tetrahydro-1H-2-benzazepin-4-acetic acid obtained in Example 5-(a) and 1.30 mL (6.26 mmol) of 1-undecyl alcohol were mixed, 12.4 mL (49.6 mmol) of 4N hydrogen chloride/1,4-dioxane solution was added to the mixture, and the resulting mixture was stirred under nitrogen gas atmosphere at 45° C. for 4 hours.

After completion of the reaction, the reaction mixture was concentrated under reduced pressure, the residue was applied to silica gel column chromatography (eluent; ethyl acetate→chloroform:methanol=19:1 (V/V)), and the separated fractions containing the desired product were concentrated under reduced pressure to obtain 527 mg of the title compound as pale yellow foam. (Yield 65%)

Mass spectrum (FAB, m/z): 621 ($M^+$+1)

$^1$H-NMR spectrum (DMSO-$d_6$, δ ppm): 0.85 (t, J=6.7 Hz, 3H), 1.21-1.31 (m, 16H), 1.50-1.58 (m, 2H), 1.94-2.02 (m, 2H), 2.63-2.76 (m, 2H), 2.89 (t, J=6.3 Hz, 2H), 3.01 (dd, $J_1$=17.3 Hz, $J_2$=3.7 Hz, 1H), 3.78-3.89 (m, 3H), 3.99 (t, J=6.5 Hz, 2H), 4.11-4.28 (m, 5H), 5.31 (d, J=16.6 Hz, 1H), 6.80-6.85 (m, 3H), 7.04 (d, J=9.5 Hz, 1H), 8.22 (brs, 1H), 12.29 (brs, 1H).

Example 9

(10-Phenyl)decyl(4S)-3-oxo-8-[2-(5,6,7,8-tetrahydroimidazo[1,2-a]pyrimidin-2-yl)-ethoxy]-2-(2,2,2-trifluoroethyl)-2,3,4,5-tetrahydro-1H-2-benzazepin-4-acetate hydrochloride 984 mg (1.74 mmol) of (4S)-3-oxo-8-[2-(8-tert-butoxycarbonyl-5,6,7,8-tetra-hydroimidazo[1,2-a]pyrimidin-2-yl)ethoxy]-2-(2,2,2-trifluoroethyl)-2,3,4,5-tetrahydro-1H-2-benzazepin-4-acetic acid obtained in Example 5-(a) and 2.12 g (8.68 mmol) of 10-phenyl-1-decyl alcohol were mixed, 17.4 mL (69.6 mmol) of 4N hydrogen chloride/1,4-dioxane solution was added to the mixture, and the resulting mixture was stirred under nitrogen gas atmosphere at 50° C. for 4 hours.

After completion of the reaction, the reaction mixture was concentrated under reduced pressure, the residue was applied to silica gel column chromatography (eluent; ethyl acetate→chloroform:methanol=19:1 (V/V)), and the separated fractions containing the desired product were concentrated under reduced pressure to obtain 815 mg of the title compound as pale yellow foam. (Yield 65%)

Mass spectrum (FAB, m/z): 683 ($M^+$+1)

$^1$H-NMR spectrum (DMSO-$d_6$, δ ppm): 1.25-1.59 (m, 16H), 1.94-2.01 (m, 2H), 2.63-2.76 (m, 2H), 2.89 (t, J=6.2 Hz, 2H), 3.00 (dd, $J_1$=17.6 Hz, $J_2$=3.9 Hz, 1H), 3.78-3.89 (m, 3H), 3.98 (t, J=6.6 Hz, 2H), 4.10-4.28 (m, 5H), 5.31 (d, J=16.4 Hz, 1H), 6.80-6.85 (m, 3H), 7.04 (d, J=9.3 Hz, 1H), 7.13-7.29 (m, 5H), 8.21 (brs, 1H), 12.23 (brs, 1H).

Example 10

[2-(Morpholin-4-yl)]ethyl(4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate hydrochloride 10-(a) [2-(Morpholin-4-yl)]ethyl(4S)-3-oxo-8-[2-(8-tert-butoxycarbonyl-5,6,7,8-tetra-hydroimidazo[1,2-a]pyrimidin-2-yl)ethoxy]-2-(2,2,2-trifluoroethyl)-2,3,4,5-tetrahydro-1H-2-benzazepin-4-acetate To 1 mL of a dichloromethane solution containing 77.4 mg (0.137 mmol) of (4S)-3-oxo-8-[2-(8-tert-butoxycarbonyl-5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetic acid obtained in Example 5-(a) were added 33 µL (0.27 mmol) of N-(2-hydroxylethyl)-morpholine, 1.7 mg (0.014 mmol) of 4-dimethylaminopyridine and 53.0 mg (0.276 mmol) of 1-ethyl-3-(3-dimethylaminopropyl)carbodiimide hydrochloride, and the resulting mixture was stirred under argon gas atmosphere at room temperature for 16 hours.

After completion of the reaction, 3 mL of dichloromethane was poured into the reaction mixture, the mixture was washed with a saturated aqueous ammonium chloride solution, a saturated aqueous sodium hydrogen carbonate solution and a saturated aqueous sodium chloride solution, dried over anhydrous magnesium sulfate, and concentrated under reduced pressure to obtain 71.7 mg of the title compound as pale yellow foam. (Yield 77%)

Mass spectrum (FAB, m/z): 680 ($M^+$+1)

$^1$H-NMR spectrum (DMSO-$d_6$, δ ppm): 1.45 (s, 9H), 1.94-2.02 (m, 2H), 2.38-2.41 (m, 4H), 2.63-2.83 (m, 4H), 3.02 (dd, $J_1$=17.2 Hz, $J_2$=4.3 Hz, 1H), 3.52-3.55 (m, 4H), 3.70-3.90 (m, 5H), 4.09-4.26 (m, 7H), 5.29 (d, J=16.4 Hz, 1H), 6.71 (s, 1H), 6.78-6.82 (m, 2H), 7.01 (d, J=9.3 Hz, 1H).

10-(b) [2-(Morpholin-4-yl)]ethyl(4S)-3-oxo-8-[2-(5,6,7,8-tetrahydroimidazo[1,2-a]pyrimidin-2-yl) ethoxy]-2-(2,2,2-trifluoroethyl)-2,3,4,5-tetrahydro-1H-2-benzazepin-4-acetate hydrochloride To 1 mL of a dichloromethane solution containing 71.7 mg (0.105 mmol) of [2-(morpholin-4-yl)]ethyl(4S)-3-oxo-8-[2-(8-tert-butoxycarbonyl-5,6,7,8-tetrahydro-imidazo[1,2-a] pyrimidin-2-yl)ethoxy]-2-(2,2,2-trifluoroethyl)-2,3,4,5-tetrahydro-1H-2-benzazepin-4-acetate obtained in Example 10-(a) was added 2.00 mL (8.00 mmol) of 4N hydrogen chloride/1,4-dioxane solution, and the resulting mixture was stirred under nitrogen gas atmosphere at room temperature for 12 hours.

After completion of the reaction, the reaction mixture was concentrated under reduced pressure, the residue was applied to silica gel column chromatography (eluent; ethyl acetate→chloroform:methanol=8:1 (V/V)), and the separated fractions containing the desired product were concentrated under reduced pressure to obtain 55.1 mg of the title compound as pale yellow foam. (Yield 80%)

Mass spectrum (FAB, m/z): 580 ($M^+$+1)

$^1$H-NMR spectrum (DMSO-$d_6$, δ ppm): 1.94-2.01 (m, 2H), 2.56-2.82 (m, 3H), 2.89 (t, J=6.1 Hz, 2H), 3.04 (dd, $J_1$=17.5 Hz, $J_2$=4.3 Hz, 1H), 3.75-3.96 (m, 7H), 4.11-4.41 (m, 7H), 5.38 (d, J=16.6 Hz, 1H), 6.80-6.86 (m, 3H), 7.05 (d, J=9.0 Hz, 1H), 8.26 (brs, 1H), 11.31 (brs, 1H), 12.35 (brs, 1H).

Example 11

(5-Methyl-2-oxo-1,3-dioxolen-4-yl)methyl(4S)-3-oxo-8-[2-(5,6,7,8-tetrahydro-imidazo[1,2-a]pyrimidin-2-yl)ethoxy]-2-(2,2,2-trifluoroethyl)-2,3,4,5-tetrahydro-1H-2-benzazepin-4-acetate hydrochloride 11-(a) (5-Methyl-2-oxo-1,3-dioxolen-4-yl)methyl (4S)-3-oxo-8-[2-(8-tert-butoxy-carbonyl-5,6,7,8-tetrahydroimidazo[1,2-a]pyrimidin-2-yl)ethoxy]-2-(2,2,2-trifluoro-ethyl)-2,3,4,5-tetrahydro-1H-2-benzazepin-4-acetate To 1.0 mL of a dimethylformamide solution containing 113 mg (0.200 mmol) of (4S)-3-oxo-8-[2-(8-tert-butoxycarbonyl-5,6,7,8-tetrahydroimidazo[1,2-a]pyrimidin-2-yl) ethoxy]-2-(2,2,2-trifluoroethyl)-2,3,4,5-tetrahydro-1H-2-benzazepin-4-acetic acid obtained in Example 5-(a) was added 21 mg (0.25 mmol) of sodium hydrogen carbonate, and the mixture was stirred under argon gas atmosphere and ice-cooling. Then, 29.7 mg (0.200 mmol) of 4-chloromethyl-5-methyl-1,3-dioxol-2-one was added to the mixture, and the resulting mixture was stirred at the same temperature for 2.5 hours. After elevating to room temperature, 55.3 mg (0.400 mmol) of potassium carbonate was added to the mixture, and the resulting mixture was stirred at room temperature for 6 hours. 7.4 mg (0.050 mmol) of 4-chloromethyl-5-methyl-1,3-dioxol-2-one was further added to the mixture, and the resulting mixture was stirred at room temperature for 15.5 hours.

After completion of the reaction, the reaction mixture was poured into 10 mL of water, and extracted with 30 mL of ethyl acetate. The organic layer was washed with a saturated aqueous sodium chloride solution, dried over anhydrous magnesium sulfate, and then, it was concentrated under reduced pressure. The obtained residue was applied to silica gel column chromatography (eluent; chloroform:methanol=39:1→25:1 (V/V)), and the separated fractions containing the desired product were concentrated under reduced pressure to obtain 116 mg of the title compound as brown oil.

(Yield 86%)

Mass spectrum (FAB, m/z): 679 ($M^+$+1).

$^1$H-NMR spectrum (CDCl$_3$, δ ppm): 1.54 (s, 9H), 2.05-2.13 (m, 2H), 2.16 (s, 3H), 2.49 (dd, $J_1$=17.0 Hz, $J_2$=4.8 Hz, 1H), 2.84-3.06 (m, 5H), 3.78-4.00 (m, 7H), 4.15-4.29 (m, 3H), 4.81 (d, J=13.8 Hz, 1H), 4.91 (d, J=13.8 Hz, 1H), 5.31 (d, J=16.4 Hz, 1H), 6.50 (s, 1H), 6.64 (d, J=2.7 Hz, 1H), 6.81 (dd, $J_1$=8.4 Hz, $J_2$=2.7 Hz, 1H), 7.00 (d, J=8.6 Hz, 1H).

11-(b) (5-Methyl-2-oxo-[1,3]dioxolen-4-yl)methyl (4S)-3-oxo-8-[2-(5,6,7,8-tetrahydro-imidazo[1,2-a]pyrimidin-2-yl)ethoxy]-2-(2,2,2-trifluoroethyl)-2,3,4,5-tetrahydro-1H-2-benzazepin-4-acetate hydrochloride To 3 mL of a dichloromethane solution containing 107 mg (0.158 mmol) of (5-methyl-2-oxo-[1,3]dioxolen-4-yl)methyl (4S)-3-oxo-8-[2-(8-tert-butoxycarbonyl-5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate obtained in Example 11-(a) was added 593 µL (2.37 mmol) of 4N hydrogen chloride/1,4-dioxane solution, and the resulting mixture was stirred under argon gas atmosphere at room temperature for 23 hours. 319 µL (1.28 mmol) of 4N hydrogen chloride/1,4-dioxane solution was further added, and the resulting mixture was stirred for 20 hours.

After completion of the reaction, the reaction mixture was concentrated under reduced pressure, and the residue was applied to silica gel column chromatography (eluent; chloroform:methanol=19:1→9:1 (V/V)). Oil obtained by concentrating the separated fractions containing the desired product under reduced pressure was dissolved in 5 mL of dichloromethane, 49 µL (0.20 mmol) of 4N hydrogen chloride/1,4-dioxane solution was added to the same, an the mixture was concentrated under reduced pressure to obtain 57.4 mg of the title compound was white foam. (Yield 59%)

Mass spectrum (FAB, m/z): 579 ($M^+$+1). $^1$H-NMR spectrum (DMSO-d$_6$, δ ppm): 1.94-2.01 (m, 2H), 2.15 (s, 3H), 2.54-2.80 (m, 3H), 2.89 (t, J=6.1 Hz, 2H), 3.01 (dd, $J_1$=17.2 Hz, $J_2$=3.5 Hz, 1H), 3.81-3.89 (m, 3H), 4.10-4.29 (m, 5H), 4.91 (d, J=14.2 Hz, 1H), 4.98 (d, J=14.2 Hz, 1H), 5.32 (d, J=16.4 Hz, 1H), 6.80-6.85 (m, 3H), 7.04 (d, J=8.8 Hz, 1H), 8.17 (brs, 1H), 12.19 (brs, 1H).

Example 12

(N,N-Dimethylaminocarbonyl)methyl(4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate hydrochloride 12-(a) (N,N-Dimethylaminocarbonyl)methyl(4S)-3-oxo-8-[2-(8-tert-butoxycarbonyl-5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate To 1 mL of a dimethylformamide solution containing 113 mg (0.200 mmol) of (4S)-3-oxo-8-[2-(8-tert-butoxycarbonyl-5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetic acid obtained in Example 5-(a) was added 55.3 mg (0.400 mmol) of potassium carbonate, and the resulting mixture was stirred under argon gas atmosphere at room temperature. Then, 26 µL (0.25 mmol) of 2-chloro-N,N-dimethylacetamide was added to the mixture, and the resulting mixture was stirred at the same temperature for 8 hours.

After completion of the reaction, the reaction mixture was poured into 10 mL of water, and extracted with 30 mL of ethyl acetate. The organic layer was washed with a saturated aqueous sodium chloride solution, dried over anhydrous magnesium sulfate, and concentrated under reduced pressure. The obtained residue was applied to silica gel column chromatography (eluent; chloroform:methanol=40:1→19:1 (V/V)), and the separated fractions containing the desired product were concentrated under reduced pressure to obtain 131 mg of the title compound as yellow oil. (Yield: quantitative)

Mass spectrum (FAB, m/z): 652 ($M^+$+1).

$^1$H-NMR spectrum (CDCl$_3$, δ ppm): 1.54 (s, 9H), 2.05-2.13 (m, 2H), 2.64 (dd, $J_1$=17.0 Hz, $J_2$=5.5 Hz, 1H), 2.84-3.17 (m, 11H), 3.82-3.98 (m, 7H), 4.15-4.26 (m, 3H), 4.64 (d, J=14.4 Hz, 1H), 4.85 (d, J=14.4 Hz, 1H), 5.31 (d, J=16.1 Hz, 1H), 6.49 (s, 1H), 6.63 (d, J=2.7 Hz, 1H), 6.80 (dd, $J_1$=8.5 Hz, $J_2$=2.7 Hz, 1H), 7.02 (d, J=8.5 Hz, 1H).

12-(b) (N,N-Dimethylaminocarbonyl)methyl(4S)-3-oxo-8-[2-(5,6,7,8-tetrahydro-imidazo[1,2-a]pyrimidin-2-yl)ethoxy]-2-(2,2,2-trifluoroethyl)-2,3,4,5-tetrahydro-1H-2-benzazepin-4-acetate hydrochloride To 4 mL of a dichloromethane solution containing 125 mg (0.192 mmol) of (N,N-dimethylaminocarbonyl)methyl(4S)-3-oxo-8-[2-(8-tert-butoxycarbonyl-5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate obtained in Example 12-(a) was added 864 µL (3.46 mmol) of 4N hydrogen chloride/1,4-dioxane solution, and the resulting mixture was stirred under under argon gas atmosphere at room temperature for 19.5 hours.

After completion of the reaction, the reaction mixture was concentrated under reduced pressure, and the residue was applied to silica gel column chromatography (eluent; chloroform:methanol=19:1→9:1 (V/V)). The separated fractions containing the desired product were concentrated under reduced pressure to obtain 50.2 mg of the title compound as white foam. (Yield 44%)

Mass spectrum (FAB, m/z): 552 ($M^+$+1).

$^1$H-NMR spectrum (DMSO-d$_6$, δ ppm): 1.93-2.01 (m, 2H), 2.55 (dd, $J_1$=16.8 Hz, $J_2$=5.9 Hz, 1H), 2.66-2.92 (m, 10H), 3.12 (dd, $J_1$=17.1 Hz, $J_2$=3.9 Hz, 1H), 3.76-3.88 (m, 3H), 4.10-4.31 (m, 5H), 4.70 (d, J=14.6 Hz, 1H), 4.81 (d, J=14.6 Hz, 1H), 5.30 (d, J=16.1 Hz, 1H), 6.76-6.85 (m, 3H), 7.05 (d, J=8.1 Hz, 1H), 7.97 (brs, 1H).

Example 13

Pivaloyloxymethyl(4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate hydrochloride 13-(a) Pivaloyloxymethyl(4S)-3-oxo-8-[2-(8-tert-butoxycarbonyl-5,6,7,8-tetrahydro-imidazo[1,2-a]pyrimidin-2-yl)ethoxy]-2-(2,2,2-trifluoroethyl)-2,3,4,5-tetrahydro-1H-2-benzazepin-4-acetate To 5 mL of an acetone solution containing 900 mg (1.59 mmol) of (4S)-3-oxo-8-[2-(8-tert-butoxycarbonyl-5,6,7,8- tetrahydroimidazo[1,2-a]pyrimidin-2-yl)ethoxy]-2-(2,2,2-trifluoroethyl)-2,3,4,5-tetrahydro-1H-2-benzazepin-4-acetic acid obtained in Example 5-(a) were added 0.66 mL (4.8 mmol) of triethylamine and 0.69 mL (4.8 mmol) of pivaloyloxymethyl chloride, and the resulting mixture was stirred at room temperature for 6 hours.

After completion of the reaction, the reaction mixture was poured into 50 ml of water, and extracted three times with 20 mL of ethyl acetate. The combined organic layers were dried over anhydrous magnesium sulfate, and the residue was applied to silica gel column chromatography (eluent; ethyl acetate→chloroform:methanol=13:1 (V/V)). The separated fractions containing the desired product were concentrated under reduced pressure to obtain 570 mg of the title compound as colorless foam.

(Yield 53%)

Mass spectrum (FAB, m/z): 681 ($M^+$+1).

$^1$H-NMR spectrum (DMSO-$d_6$, δ ppm): 1.14 (s, 9H), 1.45 (s, 9H), 1.94-2.01 (m, 2H), 2.58 (dd, $J_1$=16.8 Hz, $J_2$=4.9 Hz, 1H), 2.70-2.82 (m, 4H), 3.01 (dd, $J_1$=17.6 Hz, $J_2$=3.9 Hz, 1H), 3.69-3.73 (m, 2H), 3.80-3.90 (m, 3H), 4.10-4.23 (m, 5H), 5.30 (d, J=16.4 Hz, 1H), 5.69 (s, 2H), 6.70 (s, 1H), 6.78-6.82 (m, 2H), 7.00 (d, J=9.3 Hz, 1H).

13-(b) Pivaloyloxymethyl(4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate hydrochloride To 2 mL of a tetrahydrofuran solution containing 550 mg (0.808 mmol) of pivaloyloxymethyl(4S)-3-oxo-8-[2-(8-tert-butoxycarbonyl-5,6,7,8-tetrahydroimidazo-[1,2-a]pyrimidin-2-yl)ethoxy]-2-(2,2,2-trifluoroethyl)-2,3,4,5-tetrahydro-1H-2-benz-azepin-4-acetate obtained in Example 13-(a) were added 2 mL of acetic acid and 2 mL of water, and the resulting mixture was stirred at 50° C. for 19 hours.

After completion of the reaction, the reaction mixture was concentrated under reduced pressure, and the residue was applied to silica gel column chromatography (eluent; chloroform:methanol=14:1→9:1 (V/V)). Oil obtained by concentrating the separated fractions containing the desired product under reduced pressure was dissolved in 1.0 mL (4.0 mmol) of 4N hydrogen chloride/1,4-dioxane solution, and then, concentrated under reduced pressure to obtain 341 mg of the title compound as pale yellow foam. (Yield 68%)

Mass spectrum (FAB, m/z): 581 ($M^+$+1).

$^1$H-NMR spectrum (DMSO-$d_6$, δ ppm) 1.14 (s, 9H), 1.93-2.01 (m, 2H), 2.58 (dd, $J_1$=16.9 Hz, $J_2$=4.8 Hz, 1H), 2.65-2.81 (m, 2H), 2.89 (t, J=6.2 Hz, 2H), 3.02 (dd, $J_1$=17.3 Hz, $J_2$=3.9 Hz, 1H), 3.80-3.89 (m, 3H), 4.11-4.32 (m, 5H), 5.31 (d, J=16.4 Hz, 1H), 5.69 (s, 2H), 6.80-6.85 (m, 3H), 7.03 (d, J=9.3 Hz, 1H), 8.24 (brs, 1H), 12.32 (brs, 1H).

Test Example 1

αvβ3 Protein Binding Test

The experiment was carried out by partially modifying the method of Davis et al. (Proc. Natl. Acad. Sci., 96 (16), 9269 (1999)).

By using Echistatin (available from SIGMA Corporation), Fluorescein Amine Labeling Kit for Peptides and Proteins (available from Panvera Corporation, P2058) and Gel Filtration of Proteins Kit (P2101, available from Panvera Corporation), fluorescein isothiocyanate (hereinafter abbreviated as FITC)-Echistatin was prepared. Then, into 137 μL of Tris buffer (10 mM Tris base, 1 mM $CaCl_2$, 1 mM $MgCl_2$, 1 mM $MnCl_2$, pH 7.4), 1 μL of 200 nM FITC-Echistatin (final concentration: 1 nM) and 2 μL of 100 mg/mL bovine serum albumin (hereinafter abbreviated as BSA; available from SIGMA Corporation) (final concentration: 1 mg/mL) were mixed. To the mixture was added 10 μL of a compound to be tested, then, 50 μL of 4 nM αvβ3 (CC1019, available from CHEMICON) (final concentration: 1 nM), and the mixture was incubated at 37° C. for 30 minutes. Binding of Echistatin and αvβ3 protein was evaluated by measuring fluorescent polarization by BEACON2000 (available from Panvera Corporation). A concentration ($IC_{50}$ value) of the compound to be tested necessary for inhibiting 50% of binding of Echistatin and αvβ3 protein was calculated by using EXSAS (available from Arm Systex Co., Ltd.). The test results are shown in Table 1.

TABLE 1

| Test compound Example No. | αvβ3 protein inhibition $IC_{50}$ value (nM) |
| --- | --- |
| Example 2 | 1.2 |
| Example 3 | 1.3 |
| Example 4 | 0.6 |
| Compound A | 7.1 |

Among the compounds to be tested, Compound A is 8-[2-[6-(methylamino)-pyridin-2-yl]-1-ethoxy]-3-oxo-2-(2,2,2-trifluoroethyl)-2,3,4,5-tetrahydro-1H-2-benz-azepin-4-acetic acid which is a racemic mixture of the compound of Example 40 mentioned in WO 98/14192A, and is a control compound having an αvβ3 inhibitory activity.

In the present test, the compound of the present invention showed excellent αvβ3 inhibitory activity as compared with that of the control compound.

Test Example 2

Cell adhesion test of αvβ3 expressed cell

The experiment was carried out by partially modifying the method of Juliano et al. (Exp. Cell Res., 225(1), 132 (1996)).

Human vitronectin (available from CHEMICON) was adjusted to 10 μg/mL with phosphate buffered physiological saline (hereinafter abbreviated as PBS). This was applied onto the 96-well plate (MS9586F, available from SUMIRON) with 100 μL/well, coating was carried out at room temperature for 1 hour, and the coating solution was removed and the plate was dried. Thereafter, blocking treatment was carried out with 1.0% BSA dissolved in Dulbecco's Modified Eagle Medium (hereinafter abbreviated as DMEM) for 1 hour, washed with PBS, and the resulting material was used for the adhesion test as a coating plate. HUVEC (human umbilical endothelial cells) (available from Clonetics Corp.) cultured in endothelian cell basal medium EBM2 (available from Clonetics Corp.) containing EGM-2 SingleQuot Kit suppi. & growth factors EGM2 (available from Clonetics Corp.) and 10% fetal bovine serum (hereinafter abbreviated as FBS) were detached by using trypsin-ethylenediamine tetraacetic acid, washed by using PBS and recovered, and then, suspended in 50% human serum-containing DMEM to prepare cell suspension of HUVEC. 50% human serum-containing DMEM solutions containing HUVEC and a compound to be tested were each added to human vitronectin coating plates each in an amount of 50 μL/well to start the adhesion test.

The adhesion test was carried out in a 5% carbonic acid gas incubator (37° C.) for 1 hour. After completion of the adhesion test, the supernatant was removed by aspiration, and the plate was washed with PBS. Crystal violet staining was carried out, and the number of stained cells was measured. A concentration ($IC_{50}$ value) of the compound to be tested necessary for inhibitig 50% of binding to human vitronectin was calculated by using EXSAS (available from Arm Systex Co., Ltd.). The test results are shown in Table 2.

The adhesion test was carried out in a 5% carbonic acid gas incubator (37° C.) for 1 hour. After completion of the adhesion test, the supernatant was removed by aspiration, and the plate was washed with PBS. Crystal violet staining was carried out, and the number of stained cells was measured. A concentration ($IC_{50}$ value) of the compound to be tested necessary for inhibitig 50% of binding to human vitronectin was calculated by using EXSAS (available from Arm Systex Co., Ltd.). The test results are shown in Table 2.

TABLE 2

| Test compound Example No. | αvβ3 expressed cells adhesion inhibiting $IC_{50}$ value (nM) |
|---|---|
| Example 2 | 61 |
| Compound A | 161 |

In the present test, the compound of the present invention showed excellent αvβ3 expression cells adhesion inhibitory activity as compared with that of the control compound.

Test Example 3

Cell Adhesion Test of αvβ6 Expressed Cell

The experiment was carried out by partially modifying the method of Goodman et al. (J. Med. Chem., 45, 1045 (2002)).

Human fibronectin (available from CHEMICON) was adjusted to 100 mg/mL with PBS. This was applied on the 96-well plate (MS9586F, available from SUMIRON) with 100 μL/well, coating was carried out at room temperature for 1 hour, and the coating solution was removed and dried. Thereafter, a blocking treatment was carried out with 1.0% BSA dissolved in DMEM for 1 hour, and washed with PBS, and this was used as a coating plate in the adhesion test. HT-29 cells (available from Dainippon Sumitomo Pharma Co., Ltd.) cultured in McCoy's 5A medium containing 10% FBS were detached by using trypsin-ethylenediamine tetraacetic acid, washed with PBS and recovered. Then, the cells were suspended in DMEM to prepare a HT-29 cells suspension. DMEM solution containing the HT-29 cells and a compound to be tested were each added to human fibronectin coating plates each in an amount of 50 μL/well to start the adhesion test.

The adhesion test was carried out in a 5% carbonic acid gas incubator (37° C.) for 2 hours. After completion of the adhesion test, the supernatant was removed by aspiration, and the plates were washed with PBS. Then, Crystal violet staining was carried out, and the number of cells was measured. A concentration ($IC_{50}$ value) of the compound to be tested necessary for inhibiting 50% of binding to human fibronectin was calculated by using EXSAS (available from Arm Systex Co., Ltd.). The test results are shown in Table 3.

TABLE 3

| Test compound Example No. | αvβ6 expressed cells adhesion inhibiting $IC_{50}$ value (nM) |
|---|---|
| Example 2 | 441 |
| Example 4 | 296 |
| Compound A | >100000 |

In the presen test, the compounds of the present invention showed excellent αvβ6 expressed cells adhesion inhibitory activity as compared with the control compound.

Test Example 4

Matrigel angiogenesis test

Under ice-cooling, a liquid state Matrigel (available from BD Biosciences) was mixed with bFGF (basic fibroblast growth factor; available from PEPRO TECH) so as to have a final concentration of 4 μg/mL. To C57BL mice (Male, 8-weeks old, supplied from Charles River Laboratories Japan Inc.) which had been grouped (1 group: 5 mice) depending on their weights were subcutaneously injected to the right and left two portions of their abdomen each 0.5 mL of Matrigel under Fluothane inhalation anesthesia. After confirming that there was no disorder in mice, administration of a compound to be tested was started. The compound to be tested was dissolved in distilled water for injection, and administered orally with an administration liquid volume of 10 mL/kg in a dose of 10 mg/kg, 30 mg/kg and 100 mg/kg twice a day for 4 days. To control group (bFGF non-treated Matrigel injected, Non-administered group of the compound to be tested) and Vehicle group (bFGF treated Matrigel injected, Non-administered group of the compound to be tested), distilled water for injection was administered in the same manner. At the next day of the final administration, FITC-dextran (available from SIGMA Corporation) dissolved in physiological saline in an amount of 40 mg/mL was administered to mice under Fluothane inhalation anesthesia from common jugular vein of mouse in a dose of 5 mL/kg. After 20 minutes, Matrigel was excised from the mouse, and a weight of the excised Matrigel was measured. Then, it was crushed with 1 mL of physiological saline containing 0.5% BSA using a tissue cell crushing device (FastPrep FP100A Instrument, available from Qbiogene Inc.) and the supernatant was recovered. An amount of FITC-dextran contained in the supernatant was measured by a fluorescent plate reader (Spectra Fluor, available from TEKAN Co.). An amount of FITC-dextran extracted from the extracted Matrigel was made a blood amount in newly formed blood vessel and an inhibitiory effect on angiogenesis was evaluated. As the compound to be tested, the compound of Example 1 of the present invention was used. The test results are shown in FIG. 1.

In the present test, the compound of the present invention showed excellent activity to inhibit angiogenesis.

Utilizability In Industry

The benzazepinone compound represented by the formula (1) or a pharmaceutically acceptable salt thereof of the present invention shows excellent αv integrin receptor (particularly αvβ3, αvβ5 and αvβ6) antagonistic activity, and has excellent characteristics as a medical compound in oral absorbability or duration of the effect, etc., so that as a medicine, it is preferably useful as a medicine for treatment or prophylaxis of diseases to which αv integrin receptor relates (for example, osteoporosis, vascular restenosis, arteriosclerosis, dissecting aneurysm, transient ischemic attack, apoplectic stroke, angina pectoris, atherosclerosis, inflammatory arthritis, rheumatoid arthritis, osteoarthritis, psoriasis, ulcerative colitis, Crohn's disease, cancer, metastatic tumor growth, connective tissue overgrowth at organs, fibrosis (in particular, pulmonary fibrosis, cystic fibrosis, skin fibrosis, liver fibrosis, cirrhosis, urethrofibrosis, kidney fibrosis, cardiac fibrosis, infantile endocardial fibrosis, pancreatic fibrosis, obstacle keratinization of skin, scleroderma, multiple sclerosis, sarcoma, wound healing).

The invention claimed is:

1. A compound represented by the following structural formula (I):

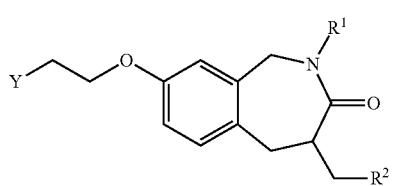

wherein $R^1$ represents a $C_1$-$C_6$ alkyl group or a halogeno $C_1$-$C_6$ alkyl group, $R^2$ is a carboxyl group which may be substituted by a $C_1$-$C_{12}$ alkyl group, $C_7$-$C_{18}$ aralkyl group, $C_1$-$C_2$ alkyl group substituted by a $C_2$-$C_5$ alkanoyloxy group, $C_1$-$C_2$ alkyl group substituted by a ($C_1$-$C_4$ alkoxy)carbonyloxy group, N,N-dimethylaminocarbonylmethyl group, 2-(morpholin-4-yl)ethyl group, (5-methyl-2-oxo-1.3-dioxolen-4-yl)methyl group or (5-phenyl-2-oxo-1,3-dioxolen-4-yl)methyl group, and Y represents the formula (II):

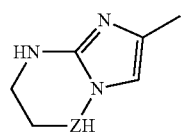

wherein Z represents CH or a nitrogen atom, or a pharmaceutically acceptable salt thereof.

2. The compound or a pharmaceutically acceptable salt thereof according to claim 1, wherein $R^1$ is a $C_1$-$C_4$ alkyl group, fluoro $C_1$-$C_4$ alkyl group or chloro $C_1$-$C_4$ alkyl group.

3. The compound or a pharmaceutically acceptable salt thereof according to claim 1, wherein $R^1$ is an ethyl group, propyl group, isopropyl group, butyl group, isobutyl group, sec-butyl group, difluoromethyl group, trifluoromethyl group, 2-fluoroethyl group, 2,2-difluoroethyl group, 2,2,2-trifluoroethyl group or 2,2,2-trichloroethyl group.

4. The compound or a pharmaceutically acceptable salt thereof according to claim 1, wherein $R^1$ is an ethyl group, difluoromethyl group, trifluoro-methyl group, 2-fluoroethyl group, 2,2-difluoroethyl group or 2,2,2-trifluoroethyl group.

5. The compound or a pharmaceutically acceptable salt thereof according to claim 1, wherein $R^1$ is an ethyl group, trifluoromethyl group or 2,2,2-trifluoroethyl group.

6. The compound or a pharmaceutically acceptable salt thereof according to claim 1, wherein $R^2$ is a carboxyl group which may be substituted by a methyl group, ethyl group, propyl group, isopropyl group, 1-ethylpropyl group, butyl group, isobutyl group, sec-butyl group, tert-butyl group, 3,3-dimethylbutyl group, pentyl group, isopentyl group, neopentyl group, tert-pentyl group, 1-methylbutyl group, hexyl group, 1-methylpentyl group, 2-methylpentyl group, 3-methylpentyl group, 1-ethylbutyl group, 2-ethylbutyl group, heptyl group, octyl group, nonyl group, decyl group, undecyl group, dodecyl group, benzyl group, phenethyl group, phenylpropyl group, phenylbutyl group, phenylpentyl group, phenylhexyl group, phenylheptyl group, phenyloctyl group, phenylnonyl group, phenyldecyl group, phenylundecyl group, phenyldodecyl group, acetoxymethyl group, 1-acetoxyethyl group, pivaloyloxymethyl group, 1-pivaloyloxyethyl group, ethoxycarbonyloxymethyl group, 1-ethoxycarbonyloxyethyl group, N,N-dimethyl-aminocarbonylmethyl group, 2-(morpholin-4-yl)ethyl group or (5-methyl-2-oxo-1.3-dioxolen-4-yl)methyl group.

7. The compound or a pharmaceutically acceptable salt thereof according to claim 1, wherein $R^2$ is a carboxyl group which may be substituted by a methyl group, ethyl group, propyl group, isopropyl group, 1-ethylpropyl grotip, butyl group, 3,3-dimethylbutyl group, pentyl group, hexyl group, heptyl group, octyl group, nonyl group, decyl group, undecyl group, dodecyl group, benzyl group, phenethyl group, phenylpropyl group, phenylbutyl group, phenylpentyl group, phenyl hexyl group, phenylheptyl group, phenyloctyl group, phenylnonyl group, phenyldecyl group, phenylundecyl group, phenyldodecyl group, acetoxymethyl group, pivaloyloxymethyl group, 1-pivaloyloxyethyl group, N,N-dimethylaminocarbonylmethyl group, 2-(morpholin-4-yl)ethyl group or (5-methyl-2-oxo-1,3-dioxolen-4-yl)methyl group.

8. The compound or a pharmaceutically acceptable salt thereof according to claim 1, wherein $R^2$ is a carboxyl group which may be substituted by an ethyl group, propyl group, isopropyl group, butyl group, pentyl group, hexyl group, heptyl group, octyl group, nonyl group, decyl group, undecyl group, benzyl group, 2-phenethyl group, 3-phenylpropyl group, 4-phenylbutyl group, 5-phenylpentyl group, 6-phenylhexyl group, 7-phenylheptyl group, 8-phenyloctyl group, 9-phenylnonyl group, 10-phenyldecyl group, pivaloyloxymethyl group, N,N-dimethylaminocarbonylmethyl group, 2-(morpholin-4-yl)ethyl group or (5-methyl-2-oxo-1,3-dioxolen-4-yl)methyl group.

9. The compound or a pharmaceutically acceptable salt thereof according to claim 1, wherein $R^1$ is a $C_1$-$C_4$ alkyl group, fluoro $C_1$-$C_4$ alkyl group.

10. The compound or a pharmaceutically acceptable salt thereof according to claim 1, wherein $R^1$ is an ethyl group, propyl group, isopropyl group, butyl group, isobutyl group, sec-butyl group, difluoromethyl group, trifluoromethyl group, 2-fluoroethyl group, 2,2-difluoroethyl group, 2,2,2-trifluoroethyl group or 2,2,2-trichloroethyl group, and $R^2$ is a carboxyl group which may be substituted by a methyl group, ethyl group, propyl group, isopropyl group, 1-ethylpropyl group, butyl group, isobutyl group, sec-butyl group, tert-butyl group, 3,3-dimethylbutyl group, pentyl group, isopentyl group, neopentyl group, tert-pentyl group, 1-methylbutyl group, hexyl group, 1-methylpentyl group, 2-methylpentyl group, 3-methylpentyl group, 1-ethylbutyl group, 2-ethylbutyl group, heptyl group, octyl group, nonyl group, decyl group, undecyl group, dodecyl group, benzyl group, phenethyl group, phenylpropyl group, phenylbutyl group, phenylpentyl group, phenylhexyl group, phenylheptyl group, phenyloctyl group, phenylnonyl group, phenyldecyl group, phenylundecyl group, phenyldodecyl group, acetoxymethyl group, 1-acetoxyethyl group, pivaloyloxymethyl group, 1-pivaloyloxyethyl group, ethoxycarbonyloxymethyl group, 1-ethoxycarbonyloxyethyl group, N,N-dimethylaminocarbonylmethyl group, 2-(morpholin-4-yl)ethyl group or (5-methyl-2-oxo-1,3-dioxolen-4-yl)methyl group.

11. The compound or a pharmaceutically acceptable salt thereof according to claim 1, wherein
R$^1$ is an ethyl group, difluoromethyl group, trifluoromethyl group, 2-fluoroethyl group, 2,2-difluoroethyl group or 2,2,2-trifluoroethyl group, and
R$^2$ is a carboxyl group which may be substituted by a methyl group, ethyl group, propyl group, isopropyl group, 1-ethylpropyl group, butyl group, 3,3-dimethylbutyl group, pentyl group, hexyl group, heptyl group, octyl group, nonyl group, decyl group, undecyl group, dodecyl group, benzyl group, phenethyl group, phenylpropyl group, phenylbutyl group, phenylpentyl group, phenylhexyl group, phenylheptyl group, phenyloctyl group, phenylnonyl group, phenyldecyl group, phenylundecyl group, phenyldodecyl group, acetoxymethyl group, pivaloyloxymethyl group, 1-pivaloyloxyethyl group, N,N-dimethylaminocarbonylmethyl group, 2-(morpholin-4-yl)ethyl group or (5-methyl-2-oxo-1,3-dioxolen-4-yl)methyl group.

12. The compound or a pharmaceutically acceptable salt thereof according to claim 1, wherein
R$^1$ is an ethyl group, trifluoromethyl group or 2,2,2-trifluoroethyl group, and
R$^2$ is a carboxyl group which may be substituted by an ethyl group, propyl group, isopropyl group, butyl group, pentyl group, hexyl group, heptyl group, octyl group, nonyl group, decyl group, undecyl group, benzyl group, 2-phenethyl group, 3-phenylpropyl group, 4-phenylbutyl group, 5-phenylpentyl group, 6-phenylhexyl group, 7-phenylheptyl group, 8-phenyloctyl group, 9-phenylnonyl group, 10-phenyldecyl group, pivaloyloxymethyl group, N,N-dimethylaminocarbonylmethyl group, 2-(morpholin-4-yl)ethyl group or (5-methyl-2-oxo-1,3-dioxolen-4-yl) methyl group.

13. The compound or a pharmaceutically acceptable salt thereof according to claim 1, wherein the compound represented by the formula (I) is represented by the following formula (III):

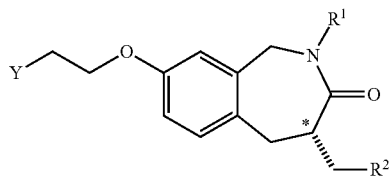

(III)

wherein the carbon atom to which * is attached has (S)-configuration.

14. The compound or a pharmaceutically acceptable salt thereof according to claim 2, wherein the compound is represented by the following formula (III):

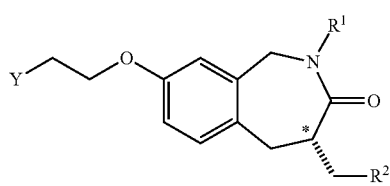

(III)

wherein the carbon atom to which * is attached has (S)-configuration.

15. The compound or a pharmaceutically acceptable salt thereof according to claim 3, wherein the compound is represented by the following formula (III):

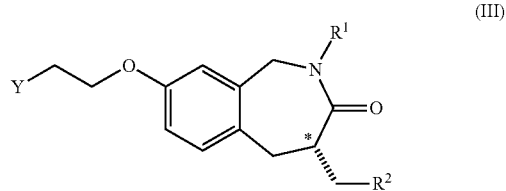

(III)

wherein the carbon atom to which * is attached has (S)-configuration.

16. The compound or a pharmaceutically acceptable salt thereof according to claim 4, wherein the compound is represented by the following formula (III):

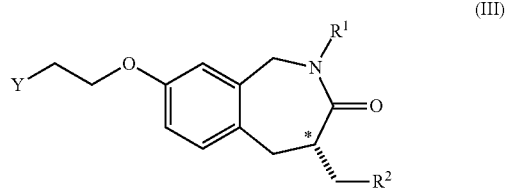

(III)

wherein the carbon atom to which * is attached has (S)-configuration.

17. The compound or a pharmaceutically acceptable salt thereof according to claim 5, wherein the compound is represented by the following formula (III):

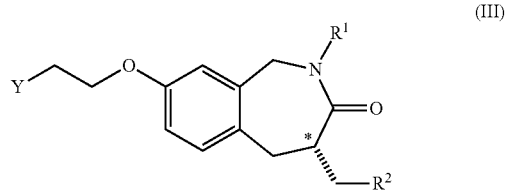

(III)

wherein the carbon atom to which * is attached has (S)-configuration.

18. The compound or a pharmaceutically acceptable salt thereof according to claim 6, wherein the compound is represented by the following formula (III):

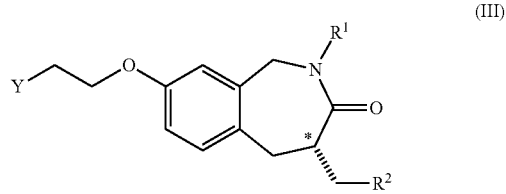

(III)

wherein the carbon atom to which * is attached has (S)-configuration.

19. The compound or a pharmaceutically acceptable salt thereof according to claim 7, wherein the compound is represented by the following formula (III):

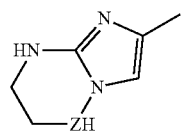
(II)

wherein the carbon atom to which * is attached has (S)-configuration.

20. The compound or a pharmaceutically acceptable salt thereof according to claim 8, wherein the compound is represented by the following formula (III):

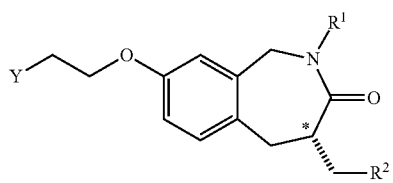
(III)

wherein the carbon atom to which * is attached has (S)-configuration.

21. The compound or a pharmaceutically acceptable salt thereof according to claim 9, wherein the compound is represented by the following formula (III):

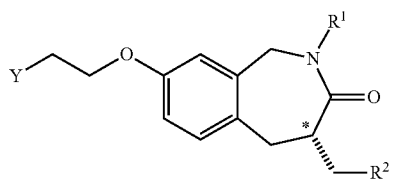
(III)

wherein the carbon atom to which * is attached has (S)-configuration.

22. The compound or a pharmaceutically acceptable salt thereof according to claim 10, wherein the compound is represented by the following formula (III):

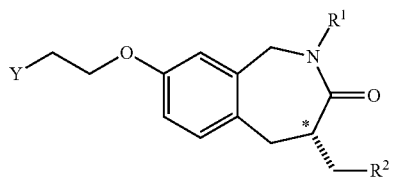
(III)

wherein the carbon atom to which * is attached has (S)-configuration.

23. The compound or a pharmaceutically acceptable salt thereof according to claim 11, wherein the compound is represented by the following formula (III):

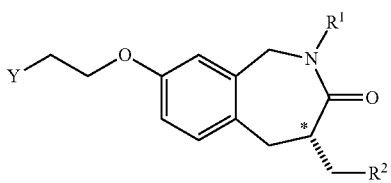
(III)

wherein the carbon atom to which * is attached has (S)-configuration.

24. The compound or a pharmaceutically acceptable salt thereof according to claim 12, wherein the compound is represented by the following formula (III):

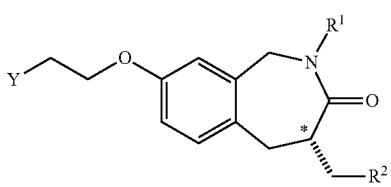
(III)

wherein the carbon atom to which * is attached has (S)-configuration.

25. The compound or a pharmaceutically acceptable salt thereof according to claim 1, wherein the compound is
3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetic acid,
(4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetic acid,
ethyl 3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate,
ethyl (4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate,
propyl 3-oxo-8-[2-(5,6,7,8-tetrahydroimidazo[1,2-a]pyrimidin-2-yl)ethoxy]-2-(2,2,2-trilluoroethyl)-2,3,4,5-tetrahydro-1H-2-benzazepin-4-acetate,
propyl (4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate,
isopropyl 3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate,
isopropyl (4S)-3-oxo-8[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate, heptyl 3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate,
heptyl (4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate,
undecyl 3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate,
undecyl (4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate, benzyl 3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate, benzyl (4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate, (10-phenyl)decyl 3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate, (10-phenyl)decyl (4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate, pivaloyloxymethyl 3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate, pivaloyloxymethyl (4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate, (N,N-dimethylaminocarbonyl)methyl 3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate, (N,N-dimethylarninocarbonyl)methyl (4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate,

[2-(morpholin-4-yl)]ethyl 3-oxo-8-[2-(5,6,7,8-tetrahydroimidazo[1,2a]pyrimidin-2-yl)ethoxy]-2-(2,2,2-trifluoroethyl)-2,3,4,5-tetrahydro-1H-2-benzazepin-4-acetate,

[2-(morpholin-4-yl)]ethyl (4S)-3-oxo-8-[2-(5,6,7,8-tetrahydroimidazo[1,2-a]pyrimidin-2-yl)ethoxy]-2-(2,2,2-trifluoroethyl)-2,3,4,5-tetrahydro-1H-2-benzazepin-4-acetate, (5-methyl-2-oxo-1,3-dioxolen-4-yl)methyl 3-oxo-8-[2-(5,6,7,8-tetrahydroi midazo[1,2-a]pyrimidin-2-yl)ethoxy]-2-(2,2,2-trifluoroethyl)-2,3,4,5-tetrahydro-1H-2-benzazepin-4-acetate, (5-methyl-2-oxo-1,3-dioxolen-4-yl)methyl (4S)-3-oxo-8-[2-(5,6,7,8-tetrahydro-imidazo[1,2-a]pyrimidin-2-yl)ethoxy]-2-(2,2,2-trifluoroethyl)-2,3,4,5-tetrahydro-1H-2-benzazepin-4-acetate, 3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetic acid, (4S)-3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetic acid, ethyl 3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, ethyl (4S)-3-oxo-8-[2-(1,2,3,4-tetrahydroimidazo[1,2-b][1,2,4]triazin-6-yl)ethoxy]-2-(2,2,2-trifltioroethyl)-2,3,4,5-tetrahydro-1H-2-benzazepin-4-acetate, propyl 3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, propyl (4S)-3-oxo-81-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, isopropyl 3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, isopropyl (4S)-3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, heptyl 3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, heptyl (4S)-3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, undecyl 3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, undecyl (4S)-3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, benzyl 3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, benzyl (4S)-3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, (10-phenyl)decyl 3-oxo-8-[2-(1,2,3,4-tetrahydroimidazo[1,2-b][1,2,4]triazin-6-yl)-ethoxy]-2-(2,2,2-trifluoroethyl)-2,3,4,5-tetrahydro-1H-2-benzazepin-4-acetate, (10-phenyl)decyl (4S)-3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, pivaloyloxymethyl 3-oxo-8-[2-(1,2,3,4-tetrahydroimidazo[1,2-b][1,2,4]triazin-6-yl)ethoxy]-2-(2,2,2-trifluorocthyl)-2,3,4,5-tetrahydro-1H-2-benzazepin-4-acetate, pivaloyloxymethyl (4S)-3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate.

(N,N-dimethylaminocarbonyl)methyl 3-oxo-8-[2-(1,2,3,4-tetrahydroimidazo[1,2-b]-[1,2,4]triazin-6-yl)ethoxy]-2-(2,2,2-trifluoroethyl)-2,3,4,5-tetrahydro-1H-2-benzazepin-4-acetate, (N,N-dimethylaminocarbonyl)methyl (4S)-3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate,

[2-(morpholin-4-yl)]ethyl 3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate,

[2-(morpholin-4-yl)]ethyl (4S)-3-oxo-8-[2-(1,2,3,4-tetrahydroi midazo[1,2-b]-[1,2,4]triazin-6-yl)ethoxy]-2-(2,2,2-trifluoroethyl)-2,3,4,5-tetrahydro-1H-2-benzazepin-4-acetate, (5-methyl-2-oxo-1,3-dioxolen-4-yl)methyl 3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate, or (5-methyl-2-oxo-1,3-dioxolen-4-yl)methyl (4S)-3-oxo-8-[2-(1,2,3,4-tetrahydroimidazo[1,2-b][1,2,4]triazin-6-yl)ethoxy]-2-(2,2,2-trifluoroethyl)-2,3,4,5-tetrahydro-1H-2-benzazepin-4-acetate.

26. A pharmaceutical composition which comprises the compound of formula (I) according to claim 1 or a pharmaceutically acceptable salt thereof as an effective ingredient.

* * * * *